United States Patent
Knoer

(10) Patent No.: US 10,053,543 B2
(45) Date of Patent: Aug. 21, 2018

(54) POLYORGANOSILOXANE GELS HAVING GLYCOSIDE GROUPS

(71) Applicant: Wacker Chemie AG, Munich (DE)

(72) Inventor: Sebastian Knoer, Emmerting (DE)

(73) Assignee: WACKER CHEMIE AG, Munich (DE)

( * ) Notice: Subject to any disclaimer, the term of this patent is extended or adjusted under 35 U.S.C. 154(b) by 138 days.

(21) Appl. No.: 15/104,053

(22) PCT Filed: Dec. 15, 2014

(86) PCT No.: PCT/EP2014/077797
§ 371 (c)(1),
(2) Date: Jun. 13, 2016

(87) PCT Pub. No.: WO2015/091378
PCT Pub. Date: Jun. 25, 2015

(65) Prior Publication Data
US 2016/0311980 A1    Oct. 27, 2016

(30) Foreign Application Priority Data

Dec. 17, 2013 (DE) ........................ 10 2013 226 252

(51) Int. Cl.
| | |
|---|---|
| *A61K 8/04* | (2006.01) |
| *A61K 8/891* | (2006.01) |
| *A61Q 19/00* | (2006.01) |
| *C08G 77/08* | (2006.01) |
| *C08G 77/14* | (2006.01) |
| *C08L 83/04* | (2006.01) |
| *C08K 5/1545* | (2006.01) |
| *C08K 5/56* | (2006.01) |
| *C08L 83/00* | (2006.01) |
| *C08G 77/12* | (2006.01) |
| *C08G 77/20* | (2006.01) |

(52) U.S. Cl.
CPC .............. *C08G 77/14* (2013.01); *A61K 8/042* (2013.01); *A61K 8/891* (2013.01); *A61Q 19/00* (2013.01); *C08G 77/08* (2013.01); *C08K 5/1545* (2013.01); *C08K 5/56* (2013.01); *C08L 83/00* (2013.01); *C08L 83/04* (2013.01); *C08G 77/12* (2013.01); *C08G 77/20* (2013.01); *C08G 2210/00* (2013.01)

(58) Field of Classification Search
CPC ........ A61K 8/042; A61K 8/891; A61Q 19/00; C08G 2210/00; C08G 77/08
See application file for complete search history.

(56) References Cited

U.S. PATENT DOCUMENTS

| | | | | |
|---|---|---|---|---|
| 5,831,080 A | * | 11/1998 | Sejpka ................... | C07H 15/04 536/120 |
| 6,365,670 B1 | * | 4/2002 | Fry ......................... | A61K 8/894 424/59 |
| 6,423,322 B1 | | 7/2002 | Fry | |
| 2003/0190301 A1 | * | 10/2003 | Fry ......................... | A61K 8/042 424/70.12 |
| 2004/0105828 A1 | * | 6/2004 | Chaiyawat ............... | A61K 8/19 424/63 |
| 2007/0276113 A1 | | 11/2007 | Fleury | |
| 2010/0330011 A1 | | 12/2010 | Kennan et al. | |
| 2015/0073059 A1 | | 3/2015 | Knoer et al. | |

FOREIGN PATENT DOCUMENTS

| | | |
|---|---|---|
| DE | 602005002262 T2 | 5/2008 |
| EP | 1132430 A1 | 9/2001 |
| WO | 2013156390 A1 | 5/2008 |

OTHER PUBLICATIONS

Ullmann's Encyclopedia of Industrial Chemistry, CD-ROM edition 2003, Wiley-VCH Verlag, heading "Emulsions".
United States Department of Health & Human Services Food and Drug Administration, Titel 21, Capital I, des Code of Federal Regulations, Part 200-299, Part 300-499.

* cited by examiner

*Primary Examiner* — Alma Pipic
(74) *Attorney, Agent, or Firm* — Brooks Kushman P.C.

(57) ABSTRACT

Organopolysiloxane gel compositions containing an organopolysiloxane gel produced by hydrosilylation of an unsaturated silicone resin and a compound containing glycoside residues and a hydrosilylatable group with at least one Si—H-functional organopolysiloxane can form creamy, storage-stable gels which are capable of containing large amounts of polar or hydrophilic substances such as water and glycerol while remaining monophasic. The compositions are especially useful in providing cosmetic compositions with a silky skinfeel.

27 Claims, No Drawings

POLYORGANOSILOXANE GELS HAVING GLYCOSIDE GROUPS

CROSS REFERENCE TO RELATED APPLICATIONS

This application is the U.S. National Phase of PCT Appln. No. PCT/EP2014/077797 filed Dec. 15, 2014, which claims priority to German Application No. 10 2013 226 252.3 filed Dec. 17, 2013, the disclosures of which are incorporated in their entirety by reference herein.

BACKGROUND OF THE INVENTION

1. Field of the Invention

The invention relates to organopolysiloxane gels having glycoside residues, to processes for production thereof and to the use thereof in cosmetic formulations.

2. Description of the Related Art

Organopolysiloxane gels can be produced by crosslinking an unsaturated organopolysiloxane resin with an Si—H-containing organopolysiloxane, also called Si—H-functional crosslinker, in the presence of a diluent.

Crosslinks are connections between polymer chains in a three-dimensional network. They may be regarded as long-chain branches that are so numerous that a continuous insoluble network or gel is formed.

Organopolysiloxane networks are frequently produced via platinum-catalyzed hydrosilylation reactions. These frequently involve reaction of an Si—H-containing organopolysiloxane and a vinyl-functional organopolysiloxane. An essential prerequisite for the formation of a 3-dimensional network here is that at least one of the two components, the Si—H-containing organopolysiloxane or the vinyl-functional organopolysiloxane, has more than two functionalities per molecule in the average composition.

The platinum-catalyzed hydrosilylation reaction offers the advantage in the formation of organopolysiloxane networks that no by-products are formed, and that linkage sites and network architecture are tightly defined.

The most important reason for the use of organopolysiloxane gels in cosmetic applications is the sensory advantages achieved thereby, more particularly the improvement in the skinfeel of cosmetic formulations. In addition, these organopolysiloxane gels serve as thickeners in cosmetic formulations.

U.S. Pat. No. 6,423,322 B1 and WO 2013/156390 A1 disclose organopolysiloxane gels which can be produced easily by hydrosilylation reaction of a specific vinyl-functional MQ resin with an Si—H-containing organopolysiloxane in the presence of a diluent and a small amount of platinum hydrosilylation catalyst. The resulting gels do not form any threads and can be homogenized easily to give a stable cream or paste. However, a disadvantage of such gels is that they have only low compatibility with polar organic substances, alcohols or water. As a result, such gels are also incapable of absorbing important cosmetic ingredients such as water or glycerol in adequate amounts, and do not show any thickening effect in aqueous or alcoholic mixtures. As a result, such gels are unsuitable or only of limited suitability for the production of water-based or alcohol-based cosmetic products.

US 2010/0330011 A1 discloses organopolysiloxane gels which are produced by crosslinking an Si—H-containing organopolysiloxane with a polyoxyalkylene having unsaturation at both ends in a diluent. The use of polyoxyalkylenes and derivatives thereof in cosmetic products is associated with great disadvantages. They are produced from highly toxic raw materials and the use thereof in cosmetic products is very controversial, since some of them are suspected of having an irritating and sensitizing effect and also of being able to make the skin permeable to other toxic substances.

EP 1 132 430 A1 discloses organopolysiloxane gels which can be produced by hydrosilylation reaction of a specific vinyl-functional MQ resin and a polyethoxylated or polypropoxylated allyl alcohol with an organopolysiloxane having a high content of Si—H bonds with about 0.5% by weight of silicon-bonded hydrogen atoms, in the presence of decamethylcyclopentasiloxane as a diluent and a small amount of platinum hydrosilylation catalyst. The resulting gels do not form any threads and can be homogenized to give a stable cream or paste. The use of a crosslinker having a high content of Si—H bonds with 0.54% by weight of Si-bonded hydrogen is described as being particularly preferred. The use of a crosslinker of lower functionality in minor amounts is said to be possible.

However, a significant disadvantage of these organopolysiloxane gels is, in particular, that the skinfeel generated is not ideal for cosmetic applications. Because of the relatively high proportion of vinyl-functional MQ resin, such gels are also comparatively costly to produce. Furthermore, it is found that it is not possible to produce suitable gels when linear organopolysiloxanes are used as diluent. However, linear organopolysiloxanes are gaining increasing significance in cosmetic formulations, since cyclic organopolysiloxanes, as used in the organopolysiloxane gels disclosed in EP 1 132 430 A1, are increasingly being avoided in cosmetic formulations because of their possibly toxic effects.

SUMMARY OF THE INVENTION

The problem addressed was that of providing organopolysiloxane gels having improved properties, especially having an improved skinfeel, and not having the abovementioned disadvantages. The problem is solved by the invention. The invention provides organopolysiloxane gels having glycoside residues, produced by reaction of (1a) unsaturated organopolysiloxane resins and
(1b) compounds having a glycoside residue and a hydrosilylatable end group,
  with the proviso that the proportion by weight, based on the total weight of the organopolysiloxane gel, is 0.1% to 10% by weight, preferably 0.1% to 5% by weight, more preferably 0.3% to 2% by weight,
with
(2) Si—H-functional organopolysiloxanes of the general formula $$H_cR_{3-c}SiO(R_2SiO)_a(RHSiO)_bSiR_{3-c}H_c \quad (I)$$

where
c is 0 or 1, preferably 0,
R may be the same or different and is a monovalent, optionally substituted hydrocarbyl radical having 1 to 18 carbon atoms per radical,
a and b are integers, with the proviso that the sum of a+b is 66 to 248, preferably 98 to 248, more preferably 118 to 168,
that the organopolysiloxanes (2) contain Si-bonded hydrogen in amounts of 0.011% to 0.044% by weight, preferably of 0.019% to 0.044% by weight, more preferably of 0.022% to 0.032% by weight,
and that the number of Si—H groups per molecule in the average composition is greater than 2 and less than 5, or mixtures of (2) Si—H-functional organopolysiloxanes with (2') Si—H-functional organopolysiloxanes of the general formula

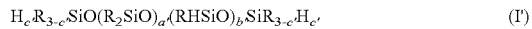

where
c' is 0 or 1, preferably 0,
R is as defined above,
a' and b' are integers, with the proviso that the sum of a'+b' is 8 to 248, preferably 38 to 248,
and that the organopolysiloxanes (2') contain Si-bonded hydrogen in amounts of 0.045% to 0.35% by weight, preferably of 0.045% to 0.156% by weight,
in the presence of
(3) catalysts that promote the addition of Si-bonded hydrogen onto aliphatic multiple bonds,
where (1a), (1b) and (2) or mixtures of (2) and (2') are dispersed in
(4) diluents, preferably organopolysiloxanes having 2 to 200 silicon atoms, preferably organopolysiloxanes having 2 to 50 silicon atoms, more preferably linear organopolysiloxanes having a viscosity of 1.5 to 50 mm$^2$/s at 25° C., or organic diluents or mixtures of organopolysiloxanes having 2 to 200 silicon atoms and organic diluents.

The invention further provides a process for producing organopolysiloxane gels of the invention by reacting
(1a) unsaturated organopolysiloxane resins and
(1b) compounds having a glycoside residue and a hydrosilylatable end group,
  with the proviso that the proportion by weight, based on the total weight of the organopolysiloxane gel, is 0.1% to 10% by weight, preferably 0.1% to 5% by weight, more preferably 0.3% to 2% by weight,
with
(2) Si—H-functional organopolysiloxanes of the general formula

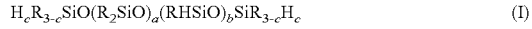

where
c is 0 or 1, preferably 0,
R may be the same or different and is a monovalent, optionally substituted hydrocarbyl radical having 1 to 18 carbon atoms per radical,
a and b are integers, with the proviso that the sum of a+b is 66 to 248, preferably 98 to 248, more preferably 118 to 168,
that the organopolysiloxanes (2) contain Si-bonded hydrogen in amounts of 0.011% to 0.044% by weight, preferably of 0.019% to 0.044% by weight, more preferably of 0.022% to 0.032% by weight,
and that the number of Si—H groups per molecule in the average composition is greater than 2 and less than 5,
or mixtures of (2) Si—H-functional organopolysiloxanes with
(2') Si—H-functional organopolysiloxanes of the general formula

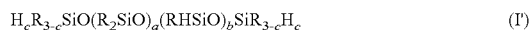

where
c is 0 or 1, preferably 0,
R is as defined above,
a and b are integers, with the proviso that the sum of a+b is 8 to 248, preferably 38 to 248,
and that the organopolysiloxanes (2') contain Si-bonded hydrogen in amounts of 0.045% to 0.35% by weight, preferably of 0.045% to 0.156% by weight,
in the presence of
(3) catalysts that promote the addition of Si-bonded hydrogen onto aliphatic multiple bonds,
where (1a), (1b) and (2) or mixtures of (2) and (2') are dispersed in
(4) diluents, preferably organopolysiloxanes having 2 to 200 silicon atoms, preferably organopolysiloxanes having 2 to 50 silicon atoms, more preferably linear organopolysiloxanes having a viscosity of 1.5 to 50 mm$^2$/s at 25° C., or organic diluents or mixtures of organopolysiloxanes having 2 to 200 silicon atoms and organic diluents.

If, in the preparation of the organopolysiloxane gels of the invention, mixtures of Si—H-functional organopolysiloxanes (2) and (2') are used, the weight ratio of (2) to (2') is preferably greater than 0.2, more preferably greater than 0.5, especially preferably greater than 1.

DETAILED DESCRIPTION OF THE PREFERRED EMBODIMENTS

It has been found that, completely surprisingly, particularly advantageous gels are obtained specifically when the organopolysiloxane gel is produced using an Si—H-containing crosslinker having a particularly low Si—H content and a glycoside residue is bonded covalently to the organopolysiloxane gel. The gels of the invention have excellent skinfeel. This result is so unexpected because sugars in general are associated more with a tacky or else a strengthening effect. Furthermore, the gels have improved compatibility with polar organic substances and are even capable of absorbing extremely hydrophilic liquids such as water or glycerol without losing the viscous gel structure.

In the context of this invention, the formulae (I) and (I') are to be understood in such a way that a —(R$_2$SiO)— units and b —(RHSiO)— units may be distributed in any desired manner in the organopolysiloxane molecule.

The Si—H-containing organopolysiloxanes (2) used in accordance with the invention preferably have a viscosity of 50 to 2000 mm$^2$/s, more preferably 100 to 1000 mm$^2$/s, and most preferably 150 to 600 mm$^2$/s, in each case at 25° C., and a molar a:(b+c) ratio of preferably 30:1 to 150:1, more preferably 30:1 to 80:1, most preferably 40:1 to 70:1. The Si—H-containing organopolysiloxanes (2') used in the mixtures with (2) as well preferably have a viscosity of 3 to 2000 mm$^2$/s, more preferably 20 to 1200 mm$^2$/s, in each case at 25° C., and a molar a:(b+c) ratio of preferably 4:1 to 30:1, more preferably 8:1 to 30:1.

It has been found that, surprisingly, the organopolysiloxane gels of the invention based on the Si—H-containing organopolysiloxanes (2) or based on the mixture of (2) and (2') have significantly better sensory properties, especially a better skinfeel, than gels based on an organopolysiloxane having a relatively high content of silicon-bonded hydrogen atoms, as disclosed in EP 1 132 430 A1. They have exceptional glidability and do not have an unwanted oily feel. After distribution on the skin, they leave a more supple skinfeel and do not leave any unwanted oily, filmlike or dull feel.

Examples of R radicals are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals, hexyl radicals such as the n-hexyl radical, heptyl radicals such as the n-heptyl radical, octyl radicals such as the n-octyl radical and isooctyl radicals such as the 2,2,4-trimethylpentyl radical, nonyl radicals such as the n-nonyl radical, decyl radicals such as the n-decyl radical, dodecyl radicals such as the n-dodecyl radical, and octadecyl radicals such as the n-octadecyl radical; cycloalkyl radicals such as cyclopentyl, cyclohexyl, cycloheptyl and methylcyclohexyl radicals; aryl radicals such as the phenyl, naphthyl, anthryl and phenanthryl radical; alkaryl radicals such as o-, m-, p-tolyl radicals, xylyl radicals and ethylphenyl radicals; and aralkyl radicals such as the benzyl radical, and the α- and the β-phenylethyl radical.

Examples of substituted R radicals are haloalkyl radicals such as the 3,3,3-trifluoro-n-propyl radical, the 2,2,2,2',2',2'-hexafluoroisopropyl radical, the heptafluoroisopropyl radical and haloaryl radicals such as the o-, m- and p-chlorophenyl radical.

Preferably, the R radical is a monovalent hydrocarbyl radical having 1 to 6 carbon atoms, particular preference being given to the methyl radical.

The unsaturated organopolysiloxane resins (1a) used in the organopolysiloxane gels of the invention are preferably unsaturated organopolysiloxane resins formed from units of the general formula (II)

$$R_xR'_ySiO_{(4-x-y)/2} \quad (II)$$

where

R is as defined above,

R' is a monovalent hydrocarbyl radical onto which may be added Si—H groups in a hydrosilylation reaction, preferably a monovalent hydrocarbyl radical having a terminal aliphatic multiple C—C bond and having 2 to 18 carbon atoms, more preferably an ω-alkenyl radical having 2 to 12 carbon atoms, most preferably a vinyl radical, x is 0, 1, 2 or 3, y is 0, 1 or 2, preferably 0 or 1, with the proviso that the sum of x+y is not more than 3, and that at least 2 R' radicals per molecule, preferably at least 3 R' radicals, at least 20 mol % of T and/or Q units (T units: sum of x+y=1; Q units: sum of x+y=0), preferably at least 20 mol % of Q units, have to be present, and D units (sum of x+y=2) may additionally be present.

Preferably, the unsaturated organopolysiloxane resins of the formula (II) are

MQ resins composed of units of the formulae

SiO$_2$(Q units) and

R$_3$SiO$_{1/2}$ and R$_2$R'SiO$_{1/2}$(M units)

where R and R' are as defined above.

The molar ratio of M to Q units is preferably in the range from 0.5 to 4.0, more preferably in the range from 0.5 to 2.0, most preferably in the range from 0.6 to 1.5. These silicone resins may also contain up to 10% by weight of free hydroxy or alkoxy groups.

Preferably, the unsaturated organopolysiloxane resins (1a) at 25° C. have a viscosity greater than 0.7 mm$^2$/s, particular preference being given to those resins which have, at 25° C., a viscosity of greater than 1000 mm$^2$/s or are solids. The weight-average molecular weight M$_w$ determined by gel permeation chromatography (based on a polystyrene standard) of these resins is preferably 334 to 200,000 g/mol, more preferably 1000 to 20,000 g/mol.

The unsaturated organopolysiloxane resins (1a) in the organopolysiloxane gels of the invention preferably have an iodine number of less than 254, and preference is given to organopolysiloxane resins having an iodine number less than 76.

The unsaturated hydrocarbyl radical is preferably bonded to an M unit (=M$_{Vi}$) or D unit (=D$_{Vi}$), preferably to an M unit, where the molar M: (M$_{Vi}$+D$_{Vi}$) ratio, preferably M:M$_{Vi}$, is preferably in the range of 0 to 50, more preferably in the range of 0 to 20, and most preferably in the range of 2.5 to 13.

Examples of R' radicals are alkenyl radicals such as the vinyl, 5-hexenyl, cyclohexenyl, 1-propenyl, allyl, 3-butenyl and 4-pentenyl radical, and alkynyl radicals such as the ethynyl, propargyl and 1-propynyl radical. Preferably, the R' radical is an alkenyl radical, more preferably an ω-alkenyl radical, and most preferably the vinyl radical.

Compounds (1b) having a glycoside residue and a hydrosilylatable end group that are used in accordance with the invention are preferably those of the general formula $$Z—(R^1O)_p—R^2 \quad (III)$$

where

Z is a glycoside residue formed from 1 to 10 monosaccharide units, preferably glucose units, R$^1$ may be the same or different and is a divalent hydrocarbyl radical having 2 to 4 carbon atoms, R$^2$ is a monovalent hydrocarbyl radical having 2 to 12 carbon atoms, onto which may be added Si—H groups in a hydrosilylation reaction, preferably a monovalent hydrocarbyl radical having a terminal aliphatic multiple C—C bond and having 2 to 12 carbon atoms, preferably 3 to 12 carbon atoms, more preferably an allyl radical, and p is 0 or an integer from 1 to 20.

Examples of compounds (1b) are

G-CH$_2$CH=CH$_2$,

G-(CH$_2$CH$_2$O)—CH$_2$CH=CH$_2$,

G$_2$-CH$_2$CH=CH$_2$,

G$_2$-(CH$_2$CH$_2$O)—CH$_2$CH=CH$_2$, where G is a glycoside residue of the formula (C$_6$H$_{11}$O$_6$)— and G$_2$ is a glycoside residue formed from two glucose units.

Preferred examples of compounds (1b) of

G-(CH$_2$CH$_2$O)—CH$_2$CH=CH$_2$ and G$_2$-(CH$_2$CH$_2$O)—CH$_2$CH=CH$_2$, where G and G$_2$ are as defined above.

U.S. Pat. No. 5,831,080 (incorporated by reference) describes organopolysiloxane compounds having glycoside residues.

Preference is given to preparing the compound (1b) by using an alkenyl glucoside, more preferably the (2-allyloxyethoxy)-glucoside of the formula

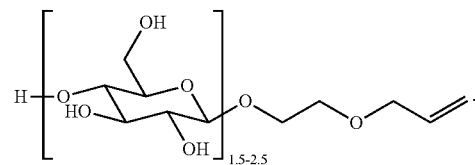

This alkenyl glucoside is prepared by the process described in U.S. Pat. No. 5,831,080 in example 1 (A) (column 8 lines 23-43), with the difference that the solvent is not entirely distilled off in the last step, since this would lead to a glassy material at room temperature, instead of which a solvent exchange to propane-1,2-diol is conducted. The product is an about 50% solution of alkenyl glucoside in propane-1,2-diol. The alkenyl glucoside is partly in condensed form as the oligoglucoside. The compounds (1b) are therefore preferably used dissolved in an organic solvent. Examples of organic solvents are alcohols such as glycerol, propane-1, 2-diol, methanol, ethanol, n-propanol and isopropanol; saturated hydrocarbons such as n-pentane, n-hexane, n-heptane and n-octane, and the branched isomers thereof, such as isododecane; benzines, for example alkane mixtures having a boiling range from 80° C. to 140° C. at 1020 hPa; unsaturated hydrocarbons such as 1-hexene, 1-heptene, 1-octene and 1-decene; aromatic hydrocarbons such as benzene, toluene and xylenes; halogenated alkanes having 1 to 6 carbon atom(s), such as methylene chloride, trichloroethylene and perchloroethylene; ethers such as di-n-butyl ether; esters such as ethyl acetate, isopropyl palmitate and isopropyl myristate; ketones such as methyl ethyl ketone and cyclohexanone.

In the organopolysiloxane gels of the invention, unsaturated organopolysiloxane resins (1a) and compounds (1b) having a glycoside residue and a hydrosilylatable end group are preferably used in amounts of 4.5 to 0.1 mol, more preferably 2 to 0.8 mol, and most preferably 1.8 to 1.1 mol, of hydrocarbyl radicals having aliphatic C—C multiple bond per mole of Si-bonded hydrogen in Si—H-functional organopolysiloxanes (2) and (2'), with the proviso that the proportion by weight of the compound (1b) is 0.1%-10% by weight, preferably 0.1%-5% by weight, more preferably 0.3%-2% by weight, based in each case on the total weight of the organopolysiloxane gel.

The weight ratio of MQ resin to the Si—H-containing organopolysiloxane in the organopolysiloxane gels disclosed in EP 1 132 430 A1 is in the range from 9 to 7. The high proportion of comparatively costly resin makes these gels comparatively costly. In the organopolysiloxane gels of the invention, the weight ratio of unsaturated organopolysiloxane resins (1) to the mixtures of the Si—H-containing organopolysiloxanes (2) and (2') is preferably in the range from 3 to 0.1, more preferably in the range of 2.5 to 0.1, and most preferably in the range of 2.0 to 0.1.

The catalysts (3) used in the process of the invention may be the same catalysts which have also been usable to date to promote the addition of Si-bonded hydrogen onto aliphatic multiple bonds. The catalysts are preferably a metal from the group of the platinum metals or a compound or a complex from the group of the platinum metals. Examples of such catalysts are metallic and finely divided platinum, which may be present on supports such as silicon dioxide, aluminum oxide or activated carbon, compounds or complexes of platinum, such as platinum halides, e.g. $PtCl_4$, $H_2PtCl_6 \cdot 6H_2O$, $Na_2PtCl_4 \cdot 4H_2O$, platinum-olefin complexes, platinum-alcohol complexes, platinum alkoxide complexes, platinum-ether complexes, platinum-aldehyde complexes, platinum-ketone complexes, including reaction products formed from $H_2PtCl_6 \cdot 6H_2O$ and cyclohexanone, platinum-vinylsiloxane complexes such as platinum-1,3-divinyl-1,1,3,3-tetramethyldisiloxane complexes with or without a content of detectable inorganically bound halogen, bis($\gamma$-picoline)-platinum dichloride, trimethylenedipyridineplatinum dichloride, dicyclopentadieneplatinum dichloride, (dimethyl sulfoxide)ethyleneplatinum(II) dichloride, cyclooctadiene-platinum dichloride, norbornadieneplatinum dichloride, $\gamma$-picolineplatinum dichloride, cyclopentadieneplatinum dichloride, and reaction products of platinum tetrachloride with olefin and primary amine or secondary amine or primary and secondary amine, such as the reaction product of platinum tetrachloride dissolved in 1-octene with sec-butylamine or ammonium-platinum complexes. Preferred hydrosilylation catalysts are platinum compounds present in a solvent suitable for use in cosmetic formulations.

Preferably, the catalyst (3) is used in amounts of 1 to 50 ppm by weight (parts per weight per million parts by weight), more preferably 2 to 20 ppm by weight, calculated in each case as elemental platinum and based on the total weight of the unsaturated organopolysiloxane resins (1), of the Si—H-functional organopolysiloxanes (2) or of the mixture of the Si—H-functional organopolysiloxanes (2) and (2') and the diluent (4).

The organopolysiloxane gels of the invention contain preferably 1% to 98% by weight of diluent, preferably 50% to 95% by weight of diluent, based on the total weight of the organopolysiloxane gels.

Unreactive or relatively unreactive diluents are preferred. In the context of the present invention, the term "unreactive" is used in relation to the crosslinking reaction in question and the reactants used therein. A relatively unreactive diluent is less than one tenth as reactive with the reactants of the crosslinking reaction as compared with the reactants with one another in the crosslinking reaction.

Suitable examples of diluents include cyclic and linear organopolysiloxanes, organic diluents and mixtures of organopolysiloxanes and organic diluents.

The organopolysiloxane may be a single organopolysiloxane or a mixture of organopolysiloxanes. The organopolysiloxane may bear alkyl, aryl, alkaryl and aralkyl groups. Such organopolysiloxanes may be illustrated by way of example by polydimethylsiloxane, polydiethylsiloxane, polymethylethylsiloxane, polymethylphenylsiloxane and polydiphenylsiloxane, but are not limited thereto.

Another possibility is the use of functional organopolysiloxanes, for example acrylamide-functional siloxane fluids, acryloyl-functional siloxane fluids, amide-functional siloxane fluids, amino-functional siloxane fluids, carbinol-functional siloxane fluids, carboxy-functional siloxane fluids, chloroalkyl-functional siloxane fluids, epoxy-functional siloxane fluids, glycol-functional siloxane fluids, ketal-functional siloxane fluids, mercapto-functional siloxane fluids, methyl ester-functional siloxane fluids, perfluoro-functional siloxane fluids and silano-functional siloxanes.

Cyclic polydimethylsiloxanes may be illustrated by way of example by hexamethylcyclotrisiloxane, octamethylcyclotetrasiloxane, decamethylcyclopentasiloxane and dodecamethylcyclohexasiloxane, but are not limited thereto.

Preferably, the organopolysiloxane is a polydimethylsiloxane having 2 to 200 silicon atoms, more preferably 2 to 50 silicon atoms, particular preference being given to linear polydimethylsiloxanes having a viscosity of 1.5 to 50 $mm^2/s$ at 25° C.

Organic diluents used may include aromatic hydrocarbons, alcohols, aldehydes, ketones, amines, esters, ethers, alkyl halides or aromatic halides. Representative examples are alcohols such as methanol, ethanol, i-propanol, cyclohexanol, benzyl alcohol, 2-octanol, ethylene glycol, propylene glycol and glycerol; aliphatic hydrocarbons such as pentane, cyclohexane, heptane, paint benzines; alkyl halides such as chloroform, carbon tetrachloride, perchloroethylene, ethyl chloride and chlorobenzene; aromatic hydrocarbons such as benzene, toluene, ethyl benzene and xylene; esters of carboxylic acids having 2 to 30 carbon atoms, such as ethyl acetate, isopropyl acetate, ethyl acetoacetate, amyl acetate, isobutyl isobutyrate, benzyl acetate, isopropyl palmitate and isopropyl myristate; ethers such as ethyl ether, n-butyl ether, tetrahydrofuran and 1,4-dioxane; ketones such as acetone, methyl ethyl ketone, cyclohexanone, diacetone alcohol, methyl amyl ketone and diisobutyl ketone; fatty oils including polyunsaturated $\omega$-3- and $\omega$-6-fatty acids, and esters thereof; vegetable oils such as peanut, olive, palm, canola, maize kernel, soya and sunflower oil and the like; and natural and synthetic oils or oil-soluble solids, such as various mono-, di- and triglycerides, polyalkoxylated vegetable oils, lanolin, lecithin and the like; and mineral oil hydrocarbons such as petrolatum, mineral oil, benzine, petroleum ether. These examples serve for illustration and should not be regarded as a restriction.

Other mixed organic diluents may also be used, such as acetonitrile, nitromethane, dimethylformamide, propylene oxide, trioctyl phosphate, butyrolactone, furfural, pine oil, turpentine and m-cresol.

Suitable organic diluents are also volatile flavoring substances such as peppermint oil, spearmint oil, menthol, vanilla, cinnamon oil, clove oil, bay oil, anise oil, eucalyptus oil, thyme oil, cedar oil, nutmeg oil, sage oil, cassia oil, cocoa, liquorice juice, starch sugar syrup from corn having a high fructose content, citrus oils such as lemon, orange, lime and grapefruit, fruit essences such as apple, pear, peach, grape, strawberry, raspberry, cherry, plum, pineapple and apricot; and other useful flavoring substances including aldehydes and esters, such as ethyl cinnamate, cinnamaldehyde, eugenyl formate, p-methylanisole, acetaldehyde, benzaldehyde, anisaldehyde, citral, neral, decanal, vanillin, tolylaldehyde, 2,6-dimethyloctanal and 2-ethylbutyraldehyde.

A portion of or the entire organic diluent may also include one or more volatile fragrances, such as natural products and perfume oils. Some representative natural products and perfume oils are amber, benzoin, cibet, clove, cedar oil, jasmine, maté, mimosa, musk, myrrh, iris, sandalwood oil and vetiver oil; aroma chemicals such as amyl salicylate, amylcinnamaldehyde, benzyl acetate, citronellol, coumarin, geraniol, isobornyl acetate, ambrette and terpinyl acetate, and various classic perfume oil families such as the flower bouquet family, the oriental family, the chypre family, the wood family, the citrus family, the canoe family, the leather family, the spice family and the herb family.

The organic diluent may also include aliphatic or alicyclic hydrocarbons having 4 to 30 carbon atoms, preferably saturated hydrocarbons. The aliphatic hydrocarbons may be straight-chain or branched, and the alicyclic hydrocarbons may be unsubstituted cyclic hydrocarbons or aliphatic hydrocarbyl-substituted hydrocarbons. Examples of suitable hydrocarbons are n-heptane, n-octane, isooctane, n-decane, isodecane, n-dodecane, isododecane, cyclohexane, cycloheptane, cyclooctane, methylcyclohexane, dimethylcyclohexane, ethylcyclohexane, nonylcyclohexane and the like. This enumeration also serves for elucidation and should not be regarded as a restriction.

Further suitable organic diluents are oil-like polyethers such as bis(alkyl) ethers of low molecular weight glycols, and liquid oligomeric and polymeric polyoxyalkylene glycols, and the alkyl mono- and diethers and mono- and dialkyl esters thereof, but the use thereof is not preferred. Preferably, the predominant portion of the polyoxyalkylene glycols is produced from a predominant portion (>50 mol %) of alkylene oxides having more than two carbon atoms, i.e. propylene oxide, 1,2- and 2,3-butylene oxide, tetrahydrofuran, oxetane, cyclohexene oxide and the like.

Preferred organic diluents have a viscosity in the range from 0.5 to 200 mm$^2$/s (25° C.), particular preference being given to those diluents having a boiling point in the range from 50° C. to 300° C.

It is possible to use numerous mixtures of diluents restricted solely to those compositions where no phase separation occurs after the production of the organopolysiloxane gel of the invention.

The production of the gel is easy to perform. In general, all constituents apart from the catalyst are added, the mixture is stirred gradually until the unsaturated organopolysiloxane resin has dissolved, and then the catalyst is added while stirring continuously. The composition can be left at room temperature until a gel has formed, or can be heated.

Preferably, the composition is heated to a temperature between 50° C. and 130° C. and preferably between 70° C. and 120° C., until the mixture gelates or solidifies. The gelation preferably proceeds within ten hours, more preferably within three hours. Organopolysiloxane gels suitable for use in cosmetic formulations are obtained.

In a particularly preferred process, in the first component step of gel production, the Si—H-functional crosslinker(s) (2) and optionally (2') and compounds (1b) having a glycoside residue and a hydrosilylatable end group are mixed. Subsequently, while stirring continuously, the catalyst is added. The mixture is preferably heated to a temperature between 50° C. and 130° C., more preferably between 70° C. and 120° C., and stirred at this temperature for 1 to 480 minutes, preferably 1 to 240 minutes, and more preferably 5 to 60 minutes. Thereafter, in the second component step of gel production, the unsaturated organopolysiloxane resin (1a) is added while stirring, and stirring is continued until the mixture gelates or solidifies. The gelation proceeds preferably within ten hours, more preferably within three hours. Organopolysiloxane gels suitable for use in cosmetic formulations are obtained.

In an alternative particularly preferred process, if two crosslinkers having a different content of Si-bonded hydrogen are used, at the start, in the first component step of gel production, just one of the two Si—H-functional crosslinkers and the compound (1b) having a glycoside residue and a hydrosilylatable end group are mixed. In the second component step of gel production, before, during or after the addition of the unsaturated organopolysiloxane resin (1a), the second Si—H-functional crosslinker is added.

In an optional second process step, the organopolysiloxane gel of the invention obtained in the first process step is homogenized using standard high-shear mixing techniques until the consistency is creamy. This can be effected by intensive mixing and dispersing in rotor-stator stirring apparatuses, colloid mills, high-pressure homogenizers, microchannels, membranes, jet nozzles and the like, or by means of ultrasound. Homogenizing equipment and methods are described, for example, in Ullmann's Encyclopedia of Industrial Chemistry, CD-ROM edition 2003, Wiley-VCH Verlag, under the heading "Emulsions".

In an optional third process step, a further amount of diluent is added to the organopolysiloxane gel obtained after the first or optional second process steps. This makes it possible, proceeding from a "base gel") obtained in the first process step, to produce a multitude of different gels which vary within a wide range in terms of consistency and their profile of properties. It is possible here to use the same diluent which has been used in the first process step, or a second diluent including those described as diluents previously herein. Alternatively, it is also possible to add any desired mixture of the diluents described previously herein and/or an active ingredient for personal care or healthcare or a mixture of an active ingredient for personal care or healthcare with one or more of the diluents described herein, with the proviso that no phase separation occurs.

An "active ingredient for personal care or healthcare" in the present context means any compound or mixture of compounds which are known in the specialist field as additives in personal care formulations and which are typically added in order to treat the hair or skin, in order to achieve a cosmetic and/or esthetic benefit, any compound or mixture of compounds which are known in the specialist field in order to achieve a pharmaceutical or medical benefit;

any compound with which pharmacological efficacy or any other effect in diagnosis, healing, alleviation, treatment or prevention of diseases is to be achieved, or in order to influence the structure or any function of the human or animal body; and any compound which can undergo a chemical change in the production of medicament products and which can be present in modified form in medicaments, in order to cause the specified efficacy or the specified effect. Thus, an "active ingredient for personal care or healthcare" encompasses an active ingredient or active medicament constituent as generally defined by the United States Department of Health & Human Services Food and Drug Administration, Title 21, Chapter I, of the Code of Federal Regulations, parts 200-299 and parts 300-499, but is not limited thereto.

The active ingredients for personal care or healthcare are preferably selected from the group of the fat- and oil-soluble vitamins, oil-soluble medicaments, particular preference being given to antiacne agents, antibacterial agents, fungicides, inflammation inhibitors, dandruff control agents, narcotics, pruritus-relieving agents, skin inflammation inhibitors and agents which are generally considered to be barrier films, and oil-soluble UV absorbers.

Useful active constituents for use in the third process step according to the invention include fat- and oil-soluble vitamins. Useful oil-soluble vitamins include, but are not limited to, vitamin $A_1$, RETINOL, $C_2$ to $C_{18}$ esters of RETINOL, vitamin E, TOCOPHEROL, esters of vitamin E and mixtures thereof. RETINOL includes trans-RETINOL, 13-cis-RETINOL, 11-cis-RETINOL, 9-cis-RETINOL and 3,4-didehydro-RETINOL. The oil-soluble vitamin may be used in the composition according to the invention in amounts of 0.01 to 50 percent by weight.

It should be noted that RETINOL is an International Nomenclature Cosmetic Ingredient Name (INCI), conferred by The Cosmetic, Toiletry and Fragrance Association (CTFA), Washington D.C., for vitamin A. Other suitable vitamins and the INCI names for the vitamins in question which are included herein are RETINYL ACETATE, RETINYL PALMITATE, RETINYL PROPIONATE, αTOCOPHEROL, TOCOPHERSOLAN, TOCOPHERYL ACETATE, TOCOPHERYL LINOLEATE, TOCOPHERYL NICOTINATE and TOCOPHERYL SUCCINATE.

Some examples of commercially available products suitable for use herein are vitamin A acetate, Fluka Chemie AG, Buchs, Switzerland; CIOVI-OX T-50, a vitamin E product from Henkel Corporation, La Grange, Ill.; COVI-OX T-70, another vitamin E product from Henkel Corporation, La Grange, Ill., and vitamin E acetate, a product from Roche Vitamins & Fine Chemicals, Nutley, N.J.

Representative examples of some suitable oil-soluble medicaments which can be added as active constituents in the third process step according to the invention are clonidine, scopolamine, propranolol, estradiol, phenylpropanolamine hydrochloride, ouabain, atropine, haloperidol, isosorbide, nitroglycerine, ibuprofen, ubiquinone, indomethacin, prostaglandins, naproxen, salbutamol, guanabenz, labetalol, pheniramine, metrifonate and steroids.

Likewise encompassed herein as a medicament for the purposes of the present invention are antiacne agents such as benzoyl peroxide, triclosan and tretinoin; antibacterial agents such as chlorhexidine gluconate; fungicides such as miconazole nitrate; inflammation inhibitors such as salicylic acid; corticosteroidal medicaments; non-steroidal inflammation inhibitors such as diclofenac; dandruff control agents such as clobetasol propionate and retinoids, narcotics such as lidocaine; pruritus-relieving agents such as polidocanol; skin inflammation inhibitors such as prednisolone, and agents which are generally regarded as barrier films.

Representative examples of oil-soluble UV absorbers which can be added as active constituents in the third process step according to the invention are 1-(4-methoxyphenyl)-3-(4-tert-butylphenyl)propane-1,3-dione (INCI: Butyl Methoxydibenzoylmethane), 2-ethylhexyl (2E)-3-(4-methoxyphenyl)prop-2-enoate (INCI: Octyl Methoxycinnamate), 4-hydroxy-2-methoxy-5-(oxophenylmethyl)benzenesulfonic acid (INCI: Benzophenone-4), 2-hydroxy-4-methoxybenzophenone-5-sulfonic acid sodium salt (INCI: Benzophenone-5) and 2-ethylhexyl 2-hydroxybenzoate (INCI: Ethylhexyl salicylate).

Preferably, in a fourth process step, the organopolysiloxane gel of the invention obtained after the first or optional second or optional third process step is homogenized using standard high-shear mixing techniques until the consistency is creamy. Technologies suitable for the purpose are mentioned above. When an additional amount of diluent has been added in the optional third process step, it is distributed homogeneously in the gel in the fourth process step. The gel swells and its softness changes.

"Creamy" in relation to the gel is understood to mean that the starting gel can be sheared until the consistency is creamy. The resulting creamy gel, according to its nature, may be pourable or comparatively stiff. The attribute "creamy" distinguishes these sheared gels, which may be transparent or opaque, from the gels produced directly by gelation of the reactive constituents.

"Storage-stable" in the context of this invention is understood to mean that the organopolysiloxane gels formed do not separate into two or more phases within 6 months of storage at room temperature and the softness of the gel does not change significantly within this period.

When mixing polar or hydrophilic solvents, such as water or glycerol, into the hydrophilically modified gels of the invention, the solvent is at first absorbed into the gel to form a monophasic homogeneous mixture, and firm creams are obtained when glycerol is used, or gelatin-like masses when water is used. If a particular amount of the polar or hydrophilic solvent is exceeded, a biphasic mixture composed of a white cream and a clear liquid is obtained, meaning that the gel is "saturated" over and above a particular amount of the polar or hydrophilic solvent and does not absorb any further amount of the appropriate polar or hydrophilic solvent.

In this aspect, the gels of the invention differ from emulsions that are dilution-stable, meaning that any desired amounts of diluent can be added, forming a lower-viscosity "milk". The gels of the invention therefore also differ from what are called "self-emulsifying elastomer gels".

A significant advantage of the organopolysiloxane gels of the invention is therefore their improved compatibility with polar or hydrophilic organic substances, for example glycerol, and even water. These important cosmetic ingredients are miscible only in very small amounts, if at all, with conventional organopolysiloxane gels. The organopolysiloxane gels of the invention are capable of absorbing extremely polar substances such as water or glycerol with retention of the viscous gel structure and formation of a monophasic homogeneous mixture. By virtue of their improved compatibility with polar and hydrophilic organic substances and even water, the organopolysiloxane gels of the invention have a thickening effect even in water- or alcohol-based formulations and impart a preferably silky skinfeel to such formulations.

The invention therefore provides monophasic homogeneous mixtures comprising (a) inventive organopolysiloxane gels having glycoside residues and
(b) polar or hydrophilic solvents.

Examples of polar or hydrophilic solvents are water, glycerol, ethylene glycol, diethylene glycol, propylene glycol and mixtures thereof, particular preference being given to water and glycerol.

The organopolysiloxane gels of the invention may absorb water preferably in amounts of at least 5% by weight, more preferably at least 10% by weight, and preferably at most 400% by weight, more preferably at most 200% by weight, based in each case on the total weight of the organopolysiloxane gels.

They can absorb glycols, preferably in amounts of at least 20% by weight, more preferably at least 25% by weight, and preferably at most 600% by weight, more preferably at most 300% by weight, based in each case on the total weight of the organopolysiloxane gels.

One skilled in the art will understand that the absorption capacity for diluents is generally limited because of the three-dimensional network structure of organopolysiloxane gels and can vary depending on the network structure and composition. If the absorption capacity for diluents has been exceeded, the formation of a diluent phase in addition to a gel phase is apparent. In the case of the organopolysiloxane gels of the invention, the general tendency is shown for the absorption capacity of hydrophilic substances to be higher in comparable gel formulations when the substitution level with compounds (1b) having a glycoside residue and a hydrosilylatable end group is higher. This opens up the possibility of controlling and optimizing the hydrophilicity of the organopolysiloxane gel of the invention according to the profile of requirements of the application.

A hydrosilylation catalyst poison or an SiH quencher is preferably added to the organopolysiloxane gel of the invention is a hydrosilylation catalyst poison or an SiH quencher, which ends the post-curing brought about as a result of remaining crosslinking hydrosilylation reactions that occur in the silicone elastomers. Examples of hydrosilylation catalyst poisons or SiH quenchers suitable for ending the post-curing are organosulfur compounds. Further suitable compounds are mentioned in U.S. Pat. No. 6,200,581. Preferred hydrosilylation catalyst poisons are mercaptoalkyl-organopolysiloxanes, particular preference being given to mercaptopropyl-functional silsesquisiloxanes or mercaptopropyl-functional polyorganosiloxanes, which are preferably used in amounts of 200 to 1.0 mol of mercapto groups per mole of platinum atoms, more preferably 50 to 1.5 mol, and most preferably 20 to 2.0 mol. The addition of the hydrosilylation catalyst poison or the SiH quencher can be effected in one or more of the process steps mentioned as desired.

The organopolysiloxane gels of the invention are suitable with particular preference for use in cosmetic applications, and are therefore preferably used in cosmetic compositions. However, they are also suitable for other applications, for example for medical and industrial applications.

The organopolysiloxane gels are of particular value in personal care products. They can be distributed gently on the skin and can therefore be used alone or mixed with other personal care product constituents, in order to form a multitude of personal care products.

Examples of personal care product constituents are esters, waxes, oils and fats of animal or vegetable origin, fatty alcohols, fatty acids, alkyl esters of fatty acids, hydrocarbons and hydrocarbon waxes, water, organic solvents, perfumes, surfactants, oil-soluble vitamins, water-soluble vitamins, oil-soluble medicaments, water-soluble medicaments, UV absorbers, active pharmaceutical compounds and others.

More particularly, the organopolysiloxane gels of the invention are suitable for antiperspirants and deodorants, since they leave a dry feel and do not cool the skin down during evaporation. They are glidable and improve the properties of skin creams, skincare lotions, moisturizers, face treatments, for example acne or wrinkle removers, body and face cleansers, bath oils, perfumes, eau de cologne, sachets, sunscreens, preshave and aftershave lotions, liquid soaps, shaving soaps and shaving foams. They can be used in hair shampoos, hair conditioners, hair sprays, mousses, permanent wave compositions, hair removers and cuticle removers, in order to improve shine and dry gliding and to provide conditioning benefits.

In cosmetics, they function as distributing agents for pigments in makeup, color cosmetics, foundation, rouge, lipsticks, lipbalm, eyeliner, mascara, grease removers and color cosmetic removers. They are suitable as administration systems for oil-soluble active constituents mentioned herein by way of example, for example vitamins, cosmetics and UV absorbers. When they are used in sticks, gels, lotions, creams, roll-ons, the elastomers impart a dry, silky smooth feel. When incorporated into cosmetics and other skincare products, the elastomers impart a matting effect.

In addition, the organopolysiloxane gels exhibit a multitude of advantageous properties, for example clarity, storage stability and simplicity of production. Therefore, they have a wide range of application, especially in antiperspirants, deodorants, skincare products, in perfumes as carriers and for hair conditioning, for example in hair balm or hair mask conditioners.

The organopolysiloxane gels have uses outside the personal care sector, including the use thereof as filler or insulation material for electrical cables, soil or water barriers for soil stabilization, or as a substitute for epoxy materials which are used in components in the electronics industry. They are likewise suitable as carriers for crosslinked silicone rubber particles. In these applications, they (i) allow simplicity of introduction of particles into such silicone phases or organic phases, such as sealants, paints, coatings, greases, adhesives, antifoams and casting resin compounds, (ii) provide modified rheological, physical or energy-absorbing properties of such phases, either in their pure state or in their final state.

In addition, the organopolysiloxane gels are capable of acting as carriers for pharmaceuticals, biocides, herbicides, pesticides and other biologically active substances.

In addition, the compositions are employed as additives for nonwoven cellulose-based carrier substrates or nonwoven synthetic carrier substrates which are used in moist cleansing tissues such as moist tissues, moist paper towels and moist hand towels, which are generally marketed for personal hygiene and domestic cleaning purposes.

The organopolysiloxane gels of the invention can be used as carriers for controlled and easily regulated release of a volatile active organic substance into the free atmosphere when they are mixed therewith. The volatile substance may especially be a perfume or an insecticide or a substance that repels insects.

In this use, the organopolysiloxane gels of the invention find wide use, for example in the modification of fibers, textiles and materials made from cotton or synthetic fibers, woven fabrics, towels, including paper towels, toilet paper or wiping paper, such as serviettes or kitchen roll, or nonwoven fabric, for long-lasting controlled fragrancing or insect repulsion. The mixture of the organopolysiloxane gels of the invention and the volatile active organic substance can also be applied in washing machines and laundry driers directly to materials and textiles as such or as an addition to washing compositions and fabric softeners.

The use of the organopolysiloxane gels of the invention as carriers for controlled and easily regulated release of a volatile active organic substance finds use especially in the abovementioned cosmetic applications, where they can bring about an additional effect to the effect described above, by releasing, for example, a perfume in a controlled manner. The organopolysiloxane gels of the invention can also be used in insect repellent preparations, where they release an insecticide or a substance that repels insects. Such products can, for example, be applied directly to the skin or the clothing.

In a further application, the mixture of the organopolysiloxane gels of the invention and the volatile active organic substance can be used for controlled fragrancing or insect repulsion in closed spaces, for example in living spaces, offices, bathrooms or motor vehicles such as buses and cars.

Gel Formulation, General Method (A and B)

According to method A, a "base gel" is first produced, which, after gelation, is diluted by addition of a further amount of diluent. Method B differs from method A basically in that the full amount of diluent is added from the start. No subsequent dilution of the gel obtained takes place.

The hydrosilylation is conducted in one step H1 or in two successive steps H1 and H2.

Method A:

A 2000 mL glass reaction vessel is equipped with a condenser having a connected nitrogen inlet, heating mantle, anchor stirrer and temperature regulator. Prior to commencement of the reaction, the reaction vessel is purged with nitrogen for 5 min. An appropriate amount of diluent, the Si—H-containing crosslinker(s) for process step H1 and (2-allyloxyethoxy)-glucoside, as a 50% solution in propane-1,2-diol, are added. Subsequently, 5 ppm of hydrosilylation catalyst are added and the reaction mixture is heated to 95° C. at a stirrer speed of about 200 rpm for 1 h. Then the optional Si—H-containing crosslinker(s) for process step H2 and then the unsaturated organopolysiloxane resin are added and the mixture is stirred until the resin has dissolved completely. 5 ppm of hydrosilylation catalyst are added and the reaction mixture is stirred at 95° C. at a stirrer speed of about 200 rpm for 2.5 hours. Subsequently, the heating mantle is removed and the mixture is cooled to room temperature at reduced stirrer speed (about 50 rpm) and catalyst poison is added. The gel obtained is homogenized while tilting with an ULTRA-TURRAX® T 50 at 6000 rpm for one minute. A "base gel" is obtained, which can have a creamy to solid or crumbly consistency and is suitable for use in cosmetic products.

For the dilution, the desired amount of diluent is added and the mixture is stirred with the anchor stirrer at 50 rpm until the diluent has been completely absorbed by the gel (about 10 minutes). Subsequently, the mixture is homogenized as again while tilting with an ULTRA-TURRAX® T 50 at 6000 rpm for one minute. In this way, a storage-stable, creamy, transparent, translucent or opaque gel with a very smooth consistency is obtained, which is suitable for use in cosmetic products.

Method B:

A 2000 mL glass reaction vessel is equipped with a condenser having a connected nitrogen inlet, heating mantle, anchor stirrer and temperature regulator. Prior to commencement of the reaction, the reaction vessel is purged with nitrogen for 5 min. The diluent, the Si—H-containing crosslinker(s) for process step H1 and (2-allyloxyethoxy)glucoside, as a 50% solution in propane-1,2-diol, are added. Subsequently, 5 ppm of hydrosilylation catalyst are added and the reaction mixture is heated to 95° C. at a stirrer speed of about 200 rpm for 1 h. Then the optional Si—H-containing crosslinker(s) for process step H2 and then the unsaturated organopolysiloxane resin are added and the mixture is stirred until the resin has dissolved completely. 5 ppm of hydrosilylation catalyst are added and the reaction mixture is stirred at 95° C. at a stirrer speed of about 200 rpm for 2.5 hours. Subsequently, the heating mantle is removed and the mixture is cooled to room temperature at reduced stirrer speed (about 50 rpm) and catalyst poison is added. The gel obtained is homogenized while tilting with an ULTRA-TURRAX® T 50 at 6000 rpm for two minutes. In this way, a storage-stable, creamy, transparent, translucent or opaque gel with a very smooth consistency is obtained, which is suitable for use in cosmetic products.

(2-Allyloxyethoxy)glucoside is prepared by the process described in U.S. Pat. No. 5,831,080 in example 1 (A) (column 8 lines 23-43).

Analytical Methods:

The viscosity of the organopolysiloxane gels was determined in accordance with DIN EN ISO 3219 at a shear rate of 1/s and 25° C.

The viscosity of the organopolysiloxanes, such as Si—H-containing crosslinker, organopolysiloxane resins and polydimethylsiloxanes, was determined in accordance with DIN 53019 in the linear range at 25° C.

The iodine number was determined in accordance with DIN 53241-1 by the method according to Wijs.

Gel permeation chromatography to determine the weight-average molecular weight Mw was conducted in accordance with ISO 16014-1 and ISO 16014-3.

Example 1-14 and Comparative Example C1-C6

According to methods A and B, a series of gels was produced. The properties of the Si—H-functional crosslinker(s) used in the examples and comparative examples are shown in table 1. Crosslinkers 1 and 2 (table 1) were added in step H1; crosslinker 3 (table 1) was added in step H2. The substances used, the amounts thereof and the properties of the gels produced are shown in tables 2 to 5 below.

TABLE 1

PROPERTIES OF THE Si—H-CONTAINING CROSSLINKERS USED IN EXAMPLES 1-14 and comparative examples C1-C6:

| No. | Distribution a: (b + c) | Sum total of a + b | Viscosity (mm$^2$/s at 25° C.) | % H |
|---|---|---|---|---|
| 1 | 2:1 | 138 | 331 | 0.47 |
| 2 | 9:1 | 60 | 58 | 0.14 |
| 3 | 55:1 | 134 | 321 | 0.026 |

Examples 1-7 are examples of inventive gels where a crosslinker having a very low content of Si—H groups is used as the sole crosslinker or in combination with a further crosslinker. The diluent chosen was a volatile linear polydimethylsiloxane (2 mm$^2$/s at 25° C.). Storage-stable, creamy gels are obtained, which are suitable for use in cosmetic formulations and can absorb significant amounts of hydrophilic liquid. Comparative examples C1, C2 and C3 show gels in the same diluent as used in examples 1-7. However, comparative example C1 contains exclusively a crosslinker having a very high content of Si—H groups, as disclosed in EP 1 132 430 A1. A low-viscosity, flowing gel having an oily feel is obtained, which is unsuitable for the applications described.

Comparative example C2 contains a crosslinker having a very high content of Si-bonded hydrogen in combination with 20% by weight of a lower-functionality crosslinker. What is obtained is not a gel but liquid. Comparative example C3 has a formulation similar to example 3, but was produced without the compound (1b) of the invention, i.e. without a compound having a glycoside residue and a hydrosilylatable end group. The gel is creamy, storage-stable and transparent, but absorbs neither water nor glycerol, as shown by comparative examples C7 (table 7) and C13 (table 8).

TABLE 2

ELASTOMER GEL FORMULATIONS:

|  |  | Example: | | | | | | |
|---|---|---|---|---|---|---|---|---|
|  |  | C1 | C2 | 1 | 2 | 3 | 4 | C3 |
| Diluent (g) | Polydimethyl-siloxane (2 mm$^2$/s)$^1$ | 760 | 770 | 760 | 760 | 760 | 770 | 810 |
| Unsaturated silicone resin$^2$ (g) |  | 206.6 | 506 | 157.4 | 118.4 | 70.4 | 118 | 90.3 |
| Si—H-containing crosslinker (g) | No. 1 (0.46% H) | 23 | 21.2 |  |  |  |  |  |
|  | No. 2 (0.14% H) |  | 5.3 | 58.9 | 32.4 |  | 32.4 |  |
|  | No. 3 (0.026% H) |  |  | 14.3 | 78.6 | 159.2 | 78.6 | 169 |
| (2-Allyloxyethoxy)glucoside (g) |  | 5 | 5 | 5 | 5 | 5 | 8 | — |
| Propane-1,2-diol (g) |  | 5 | 5 | 5 | 5 | 5 | 8 | — |
| Platinum poison (g) | Mercapto oil$^3$ | 6.9 | 6.9 | 6.9 | 6.9 | 6.9 | 6.9 | 3.8 |
| Catalyst (ppm by weight) | Platinum complex$^4$ | 5 + 5 | 5 + 5 | 5 + 5 | 5 + 5 | 5 + 5 | 5 + 5 | 5 |
| Batch size (g) |  | 1006.5 | 1019.4 | 1007.5 | 1006.3 | 1006.5 | 1021.9 | 1073.1 |
| mol of vinyl/mol of Si—H |  | 1.4 | 1.41 | 1.43 | 1.49 | 1.61 | 1.59 | 1.58 |
| Viscosity (mPa · s at 25° C.) |  | 18,800 | 1260 | 185,000 | 236,000 | 446,000 | 124,000 | 473,000 |
| Properties |  | viscous | liquid | creamy, firm | creamy, firm | creamy, firm | creamy, firm | creamy, firm |
| Appearance |  | translucent | translucent | translucent | translucent | translucent | transparent | transparent |
| Storage-stable |  | yes | yes | yes | yes | yes | yes | yes |
| % by weight of elastomer in the "base gel" (in method A) |  | — | — | — | — | — | — | — |
| % by weight of elastomer in the finished gel |  | 24 | 24 | 24 | 24 | 24 | 24 | 24 |
| Method used |  | B | B | B | B | B | B | B |

$^1$PSF-2 cSt Pure Silicone Fluid Dodecamethylpentasiloxane available from CLEARCO PRODUCTS CO. INC., U.S.A.; viscosity at 25° C.;
$^2$Ratio of M/M$^{vi}$/Q = 7.6/1/11.4, M$_n$ = 2570, M$_w$ = 5440, iodine number = 18;
$^3$Polysiloxane with 3-mercaptopropyl groups; viscosity 190 mm$^2$/s at 25° C., mercaptan content 0.29% by weight;
$^4$WACKER ® CATALYST OL available from Wacker Chemie AG;

TABLE 3

ELASTOMER GEL FORMULATIONS:

|  |  | Example: | | |
|---|---|---|---|---|
|  |  | 5 | 6 | 7 |
| Diluent (g) | Polydimethyl-siloxane (2 mm$^2$/s)$^1$ | 950 | 1250 | 1470 |
| Unsaturated silicone resin$^2$ (g) |  | 157.4 | 118.4 | 70.4 |
| Si—H-containing crosslinker (g) | No. 1 (0.46% H) |  |  |  |
|  | No. 2 (0.14% H) | 58.9 | 32.4 |  |
|  | No. 3 (0.026% H) | 14.3 | 78.6 | 159.2 |

TABLE 3-continued

ELASTOMER GEL FORMULATIONS:

|  |  | Example: | | |
|---|---|---|---|---|
|  |  | 5 | 6 | 7 |
| (2-Allyloxyethoxy)glucoside (g) |  | 5 | 5 | 5 |
| Propane-1,2-diol (g) |  | 5 | 5 | 5 |
| Platinum poison (g) | Mercapto oil[3] | 6.9 | 6.9 | 6.9 |
| Catalyst (ppm by weight) | Platinum complex[4] | 5 + 5 | 5 + 5 | 5 + 5 |
| Batch size (g) |  | 1197.5 | 1496.3 | 1006.5 |
| mol of vinyl/mol of Si—H |  | 1.43 | 1.49 | 1.61 |
| Viscosity (mPa · s at 25° C.) |  | 86,100 | 108,000 | 79,000 |
| Properties |  | creamy, firm | creamy, firm | creamy, firm |
| Appearance |  | translucent | translucent | translucent |
| Storage-stable |  | yes | yes | yes |
| % by weight of elastomer in the "base gel" (in method A) |  | 24 | 24 | 24 |
| % by weight of elastomer in the finished gel |  | 20 | 18 | 14 |
| Method used |  | A | A | A |

[1]PSF-2 cSt Pure Silicone Fluid Dodecamethylpentasiloxane available from CLEARCO PRODUCTS CO. INC., U.S.A.; viscosity at 25° C.;
[2]Ratio of $M/M^{Vi}/Q$ = 7.6/1/11.4, $M_n$ = 2570, $M_w$ = 5440, iodine number = 18;
[3]Polysiloxane having 3-mercaptopropyl groups; viscosity 190 mm$^2$/s at 25° C., mercaptan content 0.29% by weight;
[4]WACKER ® CATALYST OL available from Wacker Chemie AG;

Examples 8-14 are examples of gels where a crosslinker having a very low content of Si—H groups is used, as the sole crosslinker or in combination with a further crosslinker. The diluent chosen was nonvolatile linear polydimethylsiloxane (5 mm$^2$/s at 25° C.). Storage-stable, creamy gels are obtained, which are suitable for use in cosmetic formulations and can absorb significant amounts of hydrophilic liquid.

Comparative examples C4, C5 and C6 show gels in the same diluent as was used in examples 8-14. However, comparative example C4 contains exclusively a crosslinker having a very high content of Si—H groups, as disclosed in EP 1 132 430 A1. What is obtained is a low-viscosity, flowing gel having an oily feel, which is unsuitable for the applications described.

Comparative example C5 contains a crosslinker having a very high content of Si-bonded hydrogen in combination with 25% by weight of a lower-functionality crosslinker. What is obtained is a low-viscosity, flowing gel having an oily feel, which is unsuitable for the applications described.

Example C6 has a formulation similar to example 10, but was produced without the compound (1b) of the invention, i.e. without a compound having a glycoside residue and a hydrosilylatable end group. The gel is creamy, storage-stable and transparent, but absorbs neither water nor glycerol, as shown by comparative examples C8 (table 7) and C12 (table 8).

TABLE 4

ELASTOMER GEL FORMULATIONS:

|  |  | Example: | | | | | |
|---|---|---|---|---|---|---|---|
|  |  | C4 | C5 | 8 | 9 | 10 | 11 |
| Diluent (g) | Polydimethyl-siloxane (5 mm$^2$/s)[1] | 760 | 770 | 760 | 760 | 760 | 770 |
| Unsaturated silicone resin[2] (g) |  | 206.6 | 506 | 157.4 | 118.4 | 70.4 | 118 |
| Si—H-containing crosslinker (g) | No. 1 (0.46% H) | 23 | 21.2 |  |  |  |  |
|  | No. 2 (0.14% H) |  | 5.3 | 58.9 | 32.4 |  | 32.4 |
|  | No. 3 (0.026% H) |  |  | 14.3 | 78.6 | 159.2 | 78.6 |
| (2-Allyloxy-ethoxy)glucoside (g) |  |  | 5 | 5 | 5 | 5 | 8 |

TABLE 4-continued

ELASTOMER GEL FORMULATIONS:

|  |  | Example: | | | | | |
| --- | --- | --- | --- | --- | --- | --- | --- |
|  |  | C4 | C5 | 8 | 9 | 10 | 11 |
| Propane-1,2-diol (g) |  | 5 | 5 | 5 | 5 | 5 | 8 |
| Platinum poison (g) | Mercapto oil[3] | 6.9 | 6.9 | 6.9 | 6.9 | 6.9 | 6.9 |
| Catalyst (ppm by weight) | Platinum complex[4] | 5 + 5 | 5 + 5 | 5 + 5 | 5 + 5 | 5 + 5 | 5 + 5 |
| Batch size (g) |  | 999.6 | 1012.5 | 1000.6 | 999.4 | 999.6 | 1015.0 |
| mol of vinyl/mol of Si—H |  | 1.4 | 1.41 | 1.43 | 1.49 | 1.61 | 1.59 |
| Viscosity (mPa·s at 25° C.) |  | 14,400 | 8640 | 106,000 | 332,000 | 310,000 | 133,000 |
| Properties |  | viscous | viscous | creamy, firm | creamy, firm | creamy, firm | creamy, firm |
| Appearance |  | translucent | translucent | translucent | translucent | translucent | translucent |
| Storage-stable |  | yes | yes | yes | yes | yes | yes |
| % by weight of elastomer in the "base gel" (in method A) |  | — | — | — | — | — | — |
| % by weight of elastomer in the finished gel |  | 24 | 24 | 24 | 24 | 24 | 24 |
| Method used |  | B | B | B | B | B | B |

[1]WACKER-BELSIL ® DM 5 available from Wacker Chemie AG; viscosity at 25° C.;
[2]Ratio of M/M$^{Vi}$/Q = 7.6/1/11.4, M$_n$ = 2570, M$_w$ = 5440, iodine number = 18;
[3]Polysiloxane having 3-mercaptopropyl groups; viscosity 190 mm$^2$/s at 25° C., mercaptan content 0.29% by weight;
[4]WACKER ® CATALYST OL available from Wacker Chemie AG;

TABLE 5

ELASTOMER GEL FORMULATIONS:

|  |  | Example: | | | |
| --- | --- | --- | --- | --- | --- |
|  |  | 12 | 13 | 14 | C6 |
| Diluent (g) | Polydimethyl-siloxane (5 mm$^2$/s)[1] | 850 | 960 | 1250 | 810 |
| Unsaturated silicone resin[2] (g) |  | 157.4 | 118.4 | 70.4 | 90.3 |
| Si—H-containing crosslinker (g) | No. 1 (0.46% H) |  |  |  |  |
|  | No. 2 (0.14% H) | 58.9 | 32.4 |  |  |
|  | No. 3 (0.026% H) | 14.3 | 78.6 | 159.2 | 169 |
| (2-Allyloxyethoxy)glucoside (g) |  | 5 | 5 | 5 | — |
| Propane-1,2-diol (g) |  | 5 | 5 | 5 | — |
| Platinum poison (g) | Mercapto oil[3] | 6.9 | 6.9 | 6.9 | 3.8 |
| Catalyst (ppm by weight) | Platinum complex[4] | 5 + 5 | 5 + 5 | 5 + 5 | 5 |
| Batch size (g) |  | 1197.5 | 1496.3 | 1006.5 | 1073.1 |
| mol of vinyl/mol of Si—H |  | 1.43 | 1.49 | 1.61 | 1.58 |
| Viscosity (mPa·s at 25° C.) |  | 60,000 | 88,100 | 98,000 | 443,000 |
| Properties |  | creamy, firm | creamy, firm | creamy, firm | creamy, firm |
| Appearance |  | translucent | translucent | translucent | transparent |
| Storage-stable |  | yes | yes | yes | yes |
| % by weight of elastomer in the "base gel" (in method A) |  | 24 | 24 | 24 | — |

TABLE 5-continued

| ELASTOMER GEL FORMULATIONS: | | | | |
|---|---|---|---|---|
| | Example: | | | |
| | 12 | 13 | 14 | C6 |
| % by weight of elastomer in the finished gel | 22 | 20 | 16 | 24 |
| Method used | A | A | A | B |

[1]WACKER-BELSIL ® DM 5 available from Wacker Chemie AG; viscosity at 25° C.;
[2]Ratio of $M/M^{Vi}/Q$ = 7.6/1/11.4, $M_n$ = 2570, $M_w$ = 5440, iodine number = 18;
[3]Polysiloxane having 3-mercaptopropyl groups; viscosity 190 mm$^2$/s at 25° C., mercaptan content 0.29% by weight;
[4]WACKER ® CATALYST OL available from Wacker Chemie AG;

Examples 15-21 and Comparative Example C7-C8: Water-Containing Mixtures

The inventive organopolysiloxane gels according to examples 1-4 and 10, and the gels from comparative examples C3 and C6, were used to produce water-containing mixtures. For this purpose, variable amounts of water were added to the gels. The water was introduced into the gel in portions by shearing with an Ultra-Turrax® mixer at 1000 rpm and room temperature. The compositions and results are listed in tables 6 and 7. Examples 15, 16, 18, 20 and 21 show mono-phasic, homogeneous, stable, creamy, translucent mixtures of organopolysiloxane gel of the invention and water. Examples 17 and 19 show saturated mixtures. They are stable, translucent and creamy, but on the surface there are individual fine droplets. This is a sign that the network of the organopolysiloxane gels of the invention is saturated with solvent. The gel is now no longer able to absorb any additional water. Comparative examples C3 and C6 are creamy organopolysiloxane gels which have been produced without additional use of the compound (1b) of the invention, i.e. without a compound having a glycoside residue and a hydrosilylatable end group. They do not absorb any water and separate into two phases, a clear water phase and a clear gel phase (comparative examples C7 and C8).

TABLE 6

| aqueous mixtures: | | | | | |
|---|---|---|---|---|---|
| Example: | 15 | 16 | 17 | 18 | 19 |
| Gel from example | 1 | 2 | 2 | 3 | 3 |
| Water % by weight[1] | 11 | 11 | 18 | 11 | 25 |
| Total mass (g) | 100 | 100 | 100 | 100 | 100 |
| Mixture formed | yes | yes | yes | yes | yes |
| Viscosity (mPa · s at 25° C.) | 171,000 | 119,000 | — | 271,000 | — |
| Appearance | creamy, translucent, monophasic, homogeneous | creamy, translucent, monophasic, homogeneous | creamy, translucent, monophasic, homogeneous[2] | creamy, translucent, monophasic, homogeneous | creamy, translucent, monophasic, homogeneous[2] |

[1]% by weight of water based on the total weight of the organopolysiloxane gel.
[2]The formation of fine droplets indicates the attainment of the saturation limit.

TABLE 7

| aqueous mixtures: | | | | |
|---|---|---|---|---|
| Example: | 20 | C7 | 21 | C8 |
| Gel from example | 4 | C3 | 10 | C6 |
| Water % by weight[1] | 43 | 10 | 18 | 10 |
| Total mass (g) | 100 | 100 | 100 | 100 |

TABLE 7-continued

| aqueous mixtures: | | | | |
|---|---|---|---|---|
| Example: | 20 | C7 | 21 | C8 |
| Mixture formed | yes | no | yes | no |
| Viscosity (mPa · s at 25° C.) | 55,900 | — | 330,000 | — |
| Appearance | creamy, translucent, monophasic, homogeneous | bi-phasic, water phase clear | creamy, translucent, monophasic, homogeneous | bi-phasic, water phase clear |

[1]% by weight of water based on the total weight of the organopolysiloxane gel.

Examples 22-27 and Comparative Examples C9 and C10: Glycerol-Containing Mixtures The inventive organopolysiloxane gels according to examples 1-4, 10 and 11 and the gels from comparative examples C3 and C6 were used to produce glycerol-containing mixtures. For this purpose, variable amounts of glycerol were added to the gels. The glycerol was introduced into the gel in portions by shearing with an Ultra-Turrax® mixer at 1000 rpm and room temperature. The compositions and results are listed in table 8.

Examples 22-27 show monophasic, homogenous, stable, creamy, white mixtures of organopolysiloxane gel of the invention and glycerol. Comparative examples C3 and C6 are creamy organopolysiloxane gels which have been produced without additional use of the compound (1b) of the invention, i.e. without a compound having a glycoside residue and a hydrosilylatable end group. At first they absorb very small amounts of glycerol, i.e. less than 5% by weight, and then they separate into two phases (comparative examples C12 and C13).

TABLE 8 mixtures with glycerol:

| | Example: | | | | | | | |
|---|---|---|---|---|---|---|---|---|
| | 22 | 23 | 24 | 25 | 26 | 27 | C12 | C13 |
| Gel from example | 1 | 2 | 3 | 4 | 10 | 11 | C6 | C3 |
| Glycerol % by weight[1] | 67 | 100 | 37 | 100 | 43 | 100 | 20 | 20 |
| Total mass (g) | 100 | 100 | 100 | 100 | 100 | 100 | 100 | 100 |
| Mixture formed | yes | yes | yes | yes | yes | yes | no | no |
| Viscosity (mPa * s at 25° C.) | 295,000 | 323,000 | 358,000 | 104,000 | 597,000 | 310,000 | — | — |
| Appearance | monophasic, homogeneous, creamy, white | monophasic, homogeneous, creamy, white | monophasic, homogeneous, creamy, white | monophasic, homogeneous, creamy, white | monophasic, homogeneous, creamy, white | monophasic, homogeneous, creamy, white | biphasic | biphasic |

[1]% by weight of glycerol based on the total weight of the organopolysiloxane gel.

The organopolysiloxane gels of the invention are of excellent suitability for the production of different cosmetic products:

Example 28: Hair Mask Conditioner

A hair mask conditioner was produced using example 14 according to the following method (parts hereinafter are understood to mean parts by weight):

To an initial charge of water are added 1.5 parts of hydroxyethyl cellulose while stirring. Subsequently, 1 part of PEG-40 Hydrogenated Castor Oil is dissolved and 2 parts of example 14 added. This mixture is heated up to 75° C. During the heating, 1.5 parts of Cetyl Alcohol, 3 parts of Stearyl Alcohol, 1 part of Stearamidopropyl Dimethylamine, 3 parts of Behentrimonium Chloride, 2 parts of Glycerin and 1 part of *Simmondsia Chinensis* (Jojoba) Seed Oil are added. The mixture is stirred until 75° C. is attained and the ingredients are in dissolved form. Then the mixture is cooled. At 40° C., 0.2 parts of Citric Acid, 1 part of Ethylhexyl Methoxycinnamate, 0.1 part of *Vitis Vinifera* (Grape) Seed Oil and 0.1 part of Panthenol are added. Subsequently, the mixture is preserved with 0.1 part of Methylchloroisothiazolinone, Methylisothiazolinone. The formulation is homogenized with stirring for 5 minutes.

TABLE 9

Constituents of hair mask conditioner

| Phase | Trade name | INCI name | Parts |
|---|---|---|---|
| A | Cremophor RH 40 [1] | PEG-40 Hydrogenated Castor Oil | 1.00 |
| A | Example 14 | | 2.00 |
| A | Natrosol 250 HHR [2] | Hydroxyethylcellulose | 1.50 |
| A | Water | Aqua (DI Water) | 82.50 |
| B | Cetyl alcohol [3] | Cetyl Alcohol | 1.50 |
| B | Genamin KDMP [4] | Behentrimonium Chloride | 3.00 |
| B | Glycerol [5] | Glycerin | 2.00 |
| B | Incromine ® SD-PA-(MH) [6] | Stearamidopropyl Dimethylamine | 1.00 |
| B | Jojoba Oil Colorless [7] | *Simmondsia Chinensis* (Jojoba) Seed Oil | 1.00 |
| B | Stearyl alcohol [8] | Stearyl Alcohol | 3.00 |
| C | Citric acid [9] | Citric Acid | 0.20 |
| C | Escalol 557 [10] | Ethylhexyl Methoxycinnamate | 1.00 |
| C | Grape Seed Oil [11] | *Vitis Vinifera* (Grape) Seed Oil | 0.10 |
| C | Panthenol [12] | Panthenol | 0.10 |
| D | Kathon CG [13] | Methylchloroisothiazolinone, Methylisothiazolinone | 0.10 |

The raw materials are available from the following manufacturers:
[1] BASF AG
[2] Ashland Inc.
[3] Merck KGaA
[4] Clariant GmbH
[5] Bernd Kraft GmbH
[6] Croda GmbH
[7] Desert Whale Jojoba Co., Inc.
[8] Merck-Schuchardt
[9] Sigma
[10] Ashland Inc.
[11] Henry Lamotte GmbH
[12] BASF AG
[13] Rohm and Haas Company, Inc.

Example 29: Hair Balm

A hair balm was produced using example 14 according to the following method:

To an initial charge of 0.6 part of Aminomethyl Propanol are added 10 parts of BELSIL® P 1101. While stirring, 27.5 parts of water and 0.4 part of PEG-40 Hydrogenated Castor Oil are added. Subsequently, 2 parts of example 14 are added.

A second vessel was initially charged with 11 parts of water and 0.1 part of Disodium EDTA is dissolved while stirring. Then 3 parts of Glycerin and 0.5 parts of farnesol, linalool are added. This mixture is added to the mixture in the first vessel while stirring.

A third vessel is initially charged with 43.8 parts of water and 0.7 part of Acrylates/C10-30 Alkyl Acrylate Crosspolymer is dissolved. Then 0.1 part of Methylchloroisothiazolinone, Methylisothiazolinone and 0.3 part of perfume are added. This mixture is added to the first vessel while stirring.

TABLE 10

Constituents of hair balm

| Phase | Trade name | INCI name | Parts |
|---|---|---|---|
| A | AMP-95 [1] | Aminomethyl Propanol | 0.62 |
| A | BELSIL® P 1101 | Alcohol, Crotonic Acid/Vinyl C8-12 Isoalkyl Esters/VA/Bis-Vinyldimethicone Crosspolymer | 10.00 |
| B | Cremophor RH 40 [2] | PEG-40 Hydrogenated Castor Oil | 0.40 |
| B | Example 14 | | 2.00 |
| B | Water | Aqua (DI Water) | 27.50 |
| C | Glycerol [3] | Glycerin | 3.00 |
| C | Unistab S-69 [4] | Farnesol, Linalool | 0.50 |
| C | Versene NA [5] | Disodium EDTA | 0.10 |
| C | Water | Aqua (DI Water) | 11.00 |
| D | Carbopol Ultrez 21 [6] | Acrylates/C10-30 Alkyl Acrylate Crosspolymer | 0.70 |
| D | Kathon CG [7] | Methylchloroisothiazolinone, Methylisothiazolinone | 0.05 |
| D | Perfume | Parfum | 0.30 |
| D | Water | Aqua (DI Water) | 43.83 |

The raw materials are available from the following manufacturers:
[1] Angus Chemical Company
[2] BASF AG
[3] Bernd Kraft GmbH
[4] Induchem AG
[5] Dow Chemical USA
[6] BF Goodrich Performance Materials
[7] Rohm and Haas Company, Inc.

Example 30: Nourishing Night Cream

A nourishing night cream was produced using example 13 by the following method:

Phases A and B were weighed out separately and heated to 75° C. Phase A was added to phase B and homogenized with an Ultra Turrax T 25 basic at 15,000 revolutions per minute for 10 minutes.

The emulsion was brought to room temperature while stirring with a magnetic stirrer at 350 rpm. In the course of this, after the temperature went below 40° C., the substances of phase C were added and stirred in.

As the last component, example 13 was first stirred into the emulsion with a spatula. Thereafter, the mixture was homogenized again with the Ultra Turrax, 3 minutes at 11,000 revolutions per minute.

TABLE 11

Constituents of nourishing night cream

| Phase | INCI | Trade name (manufacturer/supplier) | Parts |
|---|---|---|---|
| A | Glycerin | Glycerol 100% anhydrous (Merck KGaA) | 5.00 |
| A | Aqua (DI Water) | Water | 52.42 |
| A | Sodium Chloride | Sodium chloride (Merck KGaA) | 1.00 |
| B | Diethylhexyl Carbonate | Tegosoft DEC (Evonik Goldschmidt GmbH) | 6.00 |
| B | *Argania Spinosa* Kernel Oil | Arganoil (Henry Lamotte GmbH) | 1.00 |
| B | Isopropyl Myristate | Isopropyl myristate (Merck-Schuchardt) | 7.00 |
| B | C12-15 Alkyl Benzoate | Tegosoft TN (Goldschmidt Chemical Corporation) | 1.00 |
| B | Coco-Caprylate | Cetiol C5 (Cognis Deutschland GmbH) | 6.00 |
| B | Polyglyceryl-2 Dipolyhydroxystearate | Dehymuls PGPH (Cognis Corporation) | 6.00 |
| B | *Vitis Vinifera* (Grape) Seed Oil | Grape Seed Oil (A & E Connock Perfumery & Cosmetics) | 3.00 |
| B | *Aloe Barbadensis* Leaf Juice | TN001 *Aloe Vera* Powder (Terry Laboratories, Inc.) | 0.03 |
| B | Magnesium Stearate | Magnesium stearate (Riedel de Haen) | 2.00 |
| B | Cera Alba | Beeswax (Fluka Chemie AG) | 3.00 |
| C | Parfum | Parfum 671 217 C Amor Girl (Fragrance Resources) | 0.25 |
| C | Phenoxyethanol, Methylparaben, Butylparaben, Ethylparaben, Propylparaben, Isobutylparaben | Euxyl K 300 (Schülke & Mayr) | 0.30 |
| D | | Example 13 | 6.00 |

Example 31: Satin Liquid Foundation SPF 10

A satin liquid foundation SPF 10 was produced using example 14 by the following method:

The oils of phase A are weighed out and stirred. The resin is stirred in with a magnetic stirrer at 350 rpm until it has dissolved. The materials of phase B are weighed into phase A and heated up to 75° C. while stirring. The water phase D is heated to 75° C. while stirring. The pigments and components of phase C are mixed with a spatula and then added to phase D while stirring. The mixture is kept at 75° C.

In a large beaker, phase C+D is homogenized with phase A+B at 75° C. with an Ultra Turrax T 25 basic at 15,000 revolutions per minute for 10 minutes. In the course of this, the homogeneous distribution of the pigments is ensured.

The emulsion was brought to room temperature while stirring with a magnetic stirrer at 350 rpm. In the course of this, after the temperature went below 40° C., the materials of phase E were added and stirred in.

As the last component, example 14 was first stirred into the emulsion with a spatula. Thereafter, the mixture is homogenized again with the Ultra Turrax, 3 minutes at 11,000 revolutions per minute.

TABLE 12

Constituents of satin liquid foundation SPF 10

| Phase | INCI | Trade name (manufacturer/supplier) | Parts |
|---|---|---|---|
| A | PPG-2 Myristyl Ether Propionate | Crodamol PMP (Croda GmbH) | 0.80 |
| A | Ethylhexyl Salicylate | Eusolex OS (Merck KGaA) | 4.80 |
| A | Trimethylsiloxysilicate | BELSIL® TMS 803 (Wacker Chemie AG) | 1.90 |
| A | Caprylic/Capric Triglyceride | Miglyol 812 N (Sasol Germany GmbH) | 1.90 |
| A | Isopropyl Myristate | Isopropyl myristate (Merck-Schuchardt) | 5.00 |
| A | Octyldodecyl Neopentanoate | Elefac I-205 (Alzo International Inc.) | 1.00 |
| B | C26-28 Alkyl Dimethicone | BELSIL® CDM 3526 VP (Wacker Chemie AG) | 1.90 |

TABLE 12-continued

Constituents of satin liquid foundation SPF 10

| Phase | INCI | Trade name (manufacturer/supplier) | Parts |
|---|---|---|---|
| B | Glyceryl Stearate SE | Tegin (Evonik Goldschmidt GmbH) | 1.90 |
| B | Butyl Methoxydibenzoylmethane | Eusolex 9020 (Merck KGaA) | 1.90 |
| B | Sorbitan Trioleate | Span 85 (Uniqema) | 1.90 |
| C | CI 77891 | Unipure White LC 981 (LCW) | 3.91 |
| C | CI 77492 | Unipure Yellow LC 181 (LCW) | 0.51 |
| C | Aluminum Starch Octenylsuccinate | Covafluid AMD (LCW) | 0.90 |
| C | Titanium Dioxide, Alumina, Simethicone | Eusolex T 2000 (Merck KGaA) | 2.90 |
| C | Magnesium Aluminum Silicate | Magnabrite S (AMCOL Health & Beauty Solution) | 0.46 |
| C | CI 77499 | Unipure Black LC 989 (LCW) | 0.03 |
| C | CI 77491 + CI 77492 + CI 77499 | Unipure Brown LC 887 (LCW) | 0.11 |
| C | CI 77491 | Unipure Red LC 383 (LCW) | 0.17 |
| C | Boron Nitride | Très BN PUHP1109 (Saint-Gobain Advanced Ceramics Boron) | 0.10 |
| C | Talc | Luzenac Pharma UM (Luzenac Europe SAS) | 1.90 |
| D | Aqua (DI Water) | Water | 48.76 |
| D | Butylene Glycol | Butane-1,3-diol | 2.90 |
| D | Glycerin | Glycerol 100% waterless (Merck KGaA) | 2.90 |
| D | Polysorbate 60 | Tween 60 (Merck KGaA) | 1.90 |
| D | Tetrasodium EDTA | EDETA B powder (BASF Corporation) | 0.30 |
| D | Xanthan Gum | Keltrol SF (CP Kelco) | 0.50 |
| E | Tocopheryl Acetate | Copherol 1250 (Cognis Corporation) | 0.30 |
| E | Parfum | Parfum SCE 243993 Pitanga (Scentec) | 0.25 |
| E | Phenoxyethanol, Methylparaben, Butylparaben, Ethylparaben, Propylparaben, Isobutylparaben | Euxyl K 300 (Schülke & Mayr) | 0.50 |
| F | | Example 14 | 7.70 |

Example 32: Anhydrous Sun Gel SPF 20

An anhydrous Sun gel SPF 20 formulation was produced using example 14 by the following method:

Phase A is stirred with a magnetic stirrer at 350 rpm for 10 minutes and heated to 75° C. until all the components have melted. Phase B is homogenized with phase A while stirring with a dissolver at 2000 revolutions per minute for 15 minutes.

The formulation was cooled down to room temperature while stirring with a dissolver. In the course of this, after the temperature went below 40° C., the materials of phase C were added and stirred in at 1000 revolutions per minute.

TABLE 13

Constituents of anhydrous sun gel SPF 20

| Phase | INCI | Trade name (manufacturer/supplier) | Parts |
|---|---|---|---|
| A | Caprylyl Methicone | Silcare Silicone 41M15 (Clariant GmbH) | 0.30 |
| A | Ethylhexyl Salicylate | Eusolex OS (Merck KGaA) | 5.00 |
| A | Polymethylsilsesquioxane | BELSIL ® PMS MK Powder (Wacker Chemie AG) | 0.70 |
| A | Diisobutyl Adipate | Crodamol Diba (Croda GmbH) | 0.70 |
| A | Octocrylene | Eusolex OCR (Merck KGaA) | 3.00 |
| A | Sorbitan Olivate | Olivem 900 (Quantiq) | 16.00 |
| A | Butyl Methoxydibenzoylmethane | Eusolex 9020 (Merck KGaA) | 1.50 |
| A | Trimethylsiloxysilicate | BELSIL ® TMS 803 (Wacker Chemie AG) | 4.00 |
| A | Ethylhexyl Methoxycinnamate | Escalol 557 (Ashland Inc.) | 7.50 |
| B | Silica Dimethyl Silylate | HDK ® H15 (Wacker Chemie AG) | 1.30 |
| C | Cyclopentasiloxane | Cyclopentasiloxane (Wacker Chemie AG) | 6.30 |
| C | | Example 14 | 26.00 |
| C | Disiloxane | BELSIL ® DM 0.65 (Wacker Chemie AG) | 4.80 |
| C | Parfum | Delight 71 028 (Fragrance Resources) | 0.20 |
| C | Dimethicone/Vinyltrimethylsiloxysilicate Crosspolymer | BELSIL ® RG 100 (Wacker Chemie AG) | 22.70 |

Example 33: Tropical Summer Butter

A tropical summer butter was produced using example 14 by the following method:

To prepare phase A, water and propanediol were mixed in a large beaker. Thereafter, xanthan gum was added gradually while stirring with a magnetic stirrer and the mixture was heated to 80-85° C. The constituents of phase B were mixed in a beaker with a magnetic stirrer and heated to 80-85° C. Phase B was added gradually to phase A and homogenized with an Ultra Turrax T 25 basic at 13,000 rpm for 10 minutes.

The formulation was cooled down to room temperature while stirring slowly with a magnetic stirrer at 350 rpm. In the course of this, after the temperature went below 40° C., the materials of phase C were added successively. Example 14 was added as the last component. Thereafter, the mixture was homogenized with an Ultra Turrax T 25 basic at 11,000 rpm for 3 minutes.

TABLE 14

Constituents of tropical summer butter

| Phase | INCI | Trade name (manufacturer/supplier) | Parts |
|---|---|---|---|
| A | Aqua (DI Water) | Water | 51.35 |
| A | Xanthan Gum | Keltrol CG-SFT (CP Kelco) | 0.20 |
| A | Propylene, Glycol | Propane-1,2-diol (BASF Corporation) | 3.00 |
| B | *Butyrospermum Parkii* (Shea Butter) | Cetiol SB 45 (Cognis Corporation) | 3.50 |
| B | *Olea Europaea* (Olive) Fruit Oil | Olive oil (Henry Lamotte GmbH) | 5.00 |

TABLE 14-continued

Constituents of tropical summer butter

| Phase | INCI | Trade name (manufacturer/supplier) | Parts |
|---|---|---|---|
| B | *Persea Gratissima* (Avocado) Oil | Avocado oil (Henry Lamotte GmbH) | 4.00 |
| B | PPG-15 Stearyl Ether | Cetiol E (BASF Corporation) | 2.50 |
| B | Cetyl Alcohol | Cetyl alcohol (Merck KGaA) | 3.50 |
| B | Ozokerite | Ozokerite | 1.00 |
| B | Steareth-2 | Eumulgin S2 (BASF Corporation) | 3.00 |
| B | C26-28 Alkyl Methicone | BELSIL ® CM 7026 VP (Wacker Chemie AG) | 2.00 |
| B | Dimethicone | BELSIL ® DM 10 (Wacker Chemie AG) | 4.00 |
| B | Dicaprylyl Ether | Cetiol OE (Cognis Corporation) | 3.00 |
| B | BHT | Ionol CP (Oxiris Chemicals S.A) | 0.05 |
| B | Cetearyl Olivate, Sorbitan Olivate | Olivem 1000 (Quantiq) | 3.00 |
| B | Isopropyl Myristate | Isopropyl myristate (Merck-Schuchardt) | 2.00 |
| B | Ceteareth-20 | Eumulgin B2 (Cognis Corporation) | 2.10 |
| C | Phenoxyethanol, Methylparaben, Butylparaben, Ethylparaben, Propylparaben, Isobutylparaben | Euxyl K 300 (Schülke & Mayr) | 0.30 |
| C | Disiloxane | BELSIL ® DM 0.65 (Wacker Chemie AG) | 2.00 |
| C | Parfum | Parfum Mangoo (Fragrance Resources) | 0.50 |
| D | | Example 14 | 4.00 |

Example 34: BB Cream

A BB cream was produced using example 14 by the following method:

The oily constituents of phase A were mixed with a magnetic stirrer at 350 rpm. Then, first of all, BELSIL® TMS 803 was added and stirring was continued until the solution was complete. Subsequently, the residual components of phase A were added. Thereafter, the constituents of phase B were added and the mixture was heated to 75° C. The constituents of phase C were mixed separately, heated to 75° C. and added gradually to phase AB. Thereafter, the mixture is homogenized with an Ultra Turrax T 25 basic 13 at 15,000 rpm. The mixture is cooled to room temperature while stirring with a magnetic stirrer at 350 rpm. In the course of this, when the temperature went below 40° C., the materials of phase D were added successively. Example 14 was added as the last component. Thereafter, the mixture was homogenized with an Ultra Turrax T 25 basic at 11,000 rpm for 3 minutes.

TABLE 15 constituents of BB cream

| Phase | INCI | Trade name (manufacturer/supplier) | Parts |
|---|---|---|---|
| A | Panthenol | D-Panthenol USP (BASF AG) | 1.00 |
| A | Butyl Methoxydibenzoylmethane | Eusolex 9020 (Merck KGaA) | 3.00 |
| A | Ethylhexyl Salicylate | Eusolex OS (Merck KGaA) | 4.00 |
| A | Polyglyceryl-2 Dipolyhydroxystearate | Dehymuls PGPH (Cognis Corporation) | 4.00 |
| A | Isododecane, Disteardimonium, Hectorite | Bentone Gel ISDV (Elementis Specialties) | 5.00 |
| A | Trimethylsiloxysilicate | BELSIL ® TMS 803 (Wacker Chemie AG) | 2.00 |
| A | Cyclopentasiloxane, Caprylyl Dimethicone Ethoxy Glucoside | BELSIL ® SPG 128 VP (Wacker Chemie AG) | 5.00 |
| A | Octocrylene | Eusolex OCR (Merck KGaA) | 10.00 |
| A | *Aloe Barbadensis* Leaf Juice | TN001 *Aloe Vera* Powder 200* Conc. (Terry Laboratories, Inc.) | 0.03 |
| A | Isopropyl Myristate | Isopropyl myristate (Merck-Schuchardt) | 4.00 |
| B | Talc, CI 77891, CI 77492, Hydrogen Dimethicone, Aluminum Hydroxide | FDP-C-Yellow3 (Prodotti Gianni S.p.A) | 0.60 |
| B | Talc, CI 77891, CI 77499, Hydrogen Dimethicone, Aluminum Hydroxide | FDP-C-Black3 (Prodotti Gianni S.p.A) | 0.15 |
| B | Talc | Talc Superiore M10 DEC (Imerys Talc) | 6.00 |
| B | Talc, CI 77891, CI 77491, Hydrogen Dimethicone, Aluminum Hydroxide | FDP-C-Red3 (Prodotti Gianni S.p.A) | 0.20 |
| B | Titanium Dioxide, Alumina, Simethicone | Eusolex T 2000 (Merck KGaA) | 5.00 |
| B | Nylon-12 (and) sodium hyaluronate | Orgasol Hydra + (Arkema) | 1.00 |
| B | Boron Nitride | Très BN PUHP500 (Saint-Gobain Advanced Ceramics Boron) | 1.00 |
| C | Glycerin | Glycerol (Bernd Kraft GmbH) | 2.50 |
| C | Sodium Chloride | Sodium chloride (Merck KGaA) | 1.00 |
| C | Aqua (DI Water) | Water | 32.02 |
| D | Phenoxyethanol, Methylparaben, Butylparaben, Ethylparaben, Propylparaben, Isobutylparaben | Euxyl K 300 (Schülke & Mayr) | 0.30 |
| D | Parfum | Parfum SCE 243993 Pitanga (Scentec) | 0.20 |
| D | Disiloxane | BELSIL ® DM 0.65 (Wacker Chemie AG) | 6.00 |
| D | Glycerin (and) Water (and) Alcohol (and) *Leontopoidum Alpinum* Extract | Alpaflor Edelweiss B. (DSM Nutritional Products AG) | 1.00 |
| E | | Example 14 | 5.00 |

Examples 35-37: Skincare Lotions Containing Examples 5-7

Three skincare lotions were produced using example 5, 6 or 7 by the following method:

Phase A is heated to 75° C. while stirring. Phase B is heated to 50° C. while stirring. Xanthan gum is allowed to run gradually into phase B. Thereafter, phase B is stirred vigorously until the phase is homogeneous and heated further to 75° C. Phase A is added gradually to phase B, while homogenization is effected with an Ultra Turrax T 25 basic at 13 rpm. The emulsion is cooled down to room temperature and the ingredients of phase C are stirred in. The elastomer gel of phase C is incorporated into the finished mixture with the Ultra Turrax T 25 basic at 11,000 rpm for 3 minutes.

TABLE 16 constituents of skincare lotion

| Phase | Trade name (manufacturer/supplier) | INCI name | Example 35 | 36 | 37 |
|---|---|---|---|---|---|
| A | Emulgade SE-PF (Cognis Corporation) | Glyceryl Stearate, Ceteareth-20, Ceteareth-12, Cetearyl Alcohol, Cetyl Palmitate | 5.00 | 5.00 | 5.00 |
| A | Isopropyl myristate (Merck-Schuchardt) | Isopropyl Myristate | 4.00 | 4.00 | 4.00 |
| A | Lanette O (Cognis Corporation) | Cetearyl Alcohol | 1.00 | 1.00 | 1.00 |
| A | Myritol 331 (Cognis Deutschland GmbH) | Cocoglycerides | 3.75 | 3.75 | 3.75 |
| A | Tegosoft DEC (Evonik Goldschmidt GmbH) | Diethylhexyl Carbonate | 3.25 | 3.25 | 3.25 |
| B | Dekaben MEP (IMCD Deutschland GmbH & Co. KG) | Phenoxyethanol, Ethylparaben, Methylparaben, Propylparaben | 0.50 | 0.50 | 0.50 |
| B | Glycerol (Bernd Kraft GmbH) | Glycerin | 3.00 | 3.00 | 3.00 |
| B | Keltrol CG-SFT (CP Kelco) | Xanthan Gum | 0.50 | 0.50 | 0.50 |
| B | Water | Aqua (DI Water) | 70.80 | 70.80 | 70.80 |
| C | Example 5 | | 8.00 | | |
| C | Example 6 | | | 8.00 | |
| C | Example 7 | | | | 8.00 |
| C | Parfum 671 217 C Amor Girl (Fragrance Resources) | Parfum | 0.20 | 0.20 | 0.20 |

Examples 38 and 39: Skincare Lotions Containing Examples 8 and 13

Two skincare lotions were produced using example 8 or 13 by the following method:

Phase A is heated to 75° C. while stirring. Phase B is heated to 50° C. while stirring. Xanthan gum is allowed to run gradually into phase B. Thereafter, phase B is stirred rigorously until the phase is homogeneous and heated further to 75° C. Phase A is added gradually to phase B, while homogenization is effected with an Ultra Turrax T 25 basic at 13 rpm. The emulsion is cooled down to room temperature and the ingredients of phase C are stirred in. The elastomer gel of phase C is incorporated into the finished mixture with the Ultra Turrax T 25 basic at 11,000 rpm for 3 minutes.

TABLE 17

Constituents of skincare lotion

| Phase | Trade name (manufacturer/supplier) | INCI name | Example 38 | 39 |
|---|---|---|---|---|
| A | Emulgade SE-PF (Cognis Corporation) | Glyceryl Stearate, Ceteareth-20, Ceteareth-12, Cetearyl Alcohol, Cetyl Palmitate | 5.00 | 5.00 |

TABLE 17-continued

Constituents of skincare lotion

| Phase | Trade name (manufacturer/supplier) | INCI name | Example 38 | 39 |
|---|---|---|---|---|
| A | Isopropyl myristate (Merck-Schuchardt) | Isopropyl Myristate | 4.00 | 4.00 |
| A | Lanette O (Cognis Corporation) | Cetearyl Alcohol | 1.00 | 1.00 |
| A | Myritol 331 (Cognis Deutschland GmbH) | Cocoglycerides | 3.75 | 3.75 |
| A | Tegosoft DEC (Evonik Goldschmidt GmbH) | Diethylhexyl Carbonate | 3.25 | 3.25 |
| B | Dekaben MEP (IMCD Deutschland GmbH & Co. KG) | Phenoxyethanol, Ethylparaben, Methylparaben, Propylparaben | 0.50 | 0.50 |
| B | Glycerol (Bernd Kraft GmbH) | Glycerin | 3.00 | 3.00 |
| B | Keltrol CG-SFT (CP Kelco) | Xanthan Gum | 0.25 | 0.25 |
| B | Water | Aqua (DI Water) | 71.05 | 71.25 |
| C | Example 8 | | 8.00 | |
| C | Example 13 | | | 8.00 |
| C | Parfum 671 217 C Amor Girl (Fragrance Resources) | Parfum | 0.20 | 0.20 |

Organopolysiloxane gels bring about sensory advantages in cosmetic applications by improving the distributability of the product on the skin and imparting a silky smooth feel to the product. A particularly advantageous viscosity for this purpose has been found to be in the range of 75,000-120,000 mPa·s at 25° C. The sensory properties were assessed by a trained group of 5 subjects.

Example 40: Sensory Assessment of the Organopolysiloxane Gels from Examples 5, 6 and 13 and Comparative Example C1 and C4

The panelists applied 0.05 g in each case of the product to the cleaned lower arm over a circular area of 20 cm$^2$, and the organopolysiloxane gels were compared with respect to their distributability relative to one another. The application was effected with the index finger or middle finger and a speed of rotation of two revolutions per second. A total of 30 revolutions were conducted. After a wait time of 60 seconds, the residues of the organopolysiloxane gels were compared with respect to their silkiness relative to one another.

The organopolysiloxane gels from examples 5 and 6 and comparative example C1 contain volatile, linear polydimethylsiloxane (2 mm$^2$/s at 25° C.) as diluent. The organopolysiloxane gel from example 13 and comparative example C4 contain nonvolatile linear polydimethylsiloxane (5 mm$^2$/s at 25° C.) as diluent. Since this results in different characteristics in the application and in the residue, the products with different diluents were each assessed separately from one another.

According to the assessment of the panelists, both of examples 5 and 6 have very good distributability. The majority of the residues of both examples were classified as silky. Example 6 was classified as being somewhat better compared to example 5 in both features.

Comparative example C1 could not be subjected to the test in a regular manner, since the material has not formed a firm gel and, because of its unsuitable flowing nature, after application to the skin, runs of its own accord. Comparative example C1, by contrast with example 5 and example 6, does not leave a matt silky film, but leaves an oily shiny layer which was not assessed as silky by any of the panelists.

TABLE 18

Sensory assessment of the organopolysiloxane gels from examples 5 and 6 and comparative example C1

| Example | Viscosity [mPa * s at 25° C.] | Solids content [%] | Distributability | Silkiness |
|---|---|---|---|---|
| 5 | 86,000 | 20 | + | + |
| 6 | 108,000 | 18 | ++ | ++ |
| C1 | 18,800 | 24 | −* | −* |

*It was not possible to test comparative example C1 in a regular manner, since the product does not have a gel-like consistency and runs on the skin of its own accord even prior to manual distribution.

According to the assessment of the panelists, example 13 has very good distributability. The residue was classified as silky by the majority. Comparative example C4 could not be subjected to the test in a regular manner, since the material has not formed a firm gel and, because of its unsuitable flowing nature, after application to the skin, flows of its own accord. Comparative example C4, by contrast with example 13, does not leave a matt silky film, but leaves an oily shiny layer which was not assessed as silky by any of the panelists.

TABLE 19

Sensory assessment of the organopolysiloxane gel from example 13 and comparative example C4

| Example | Viscosity [mPa * s at 25° C.] | Solids content [%] | Distributability | Silkiness |
|---|---|---|---|---|
| 13 | 88,100 | 20 | ++ | ++ |
| C4 | 14,400 | 24 | −* | −* |

*It was not possible to test comparative example C4 in a regular manner, since the product does not have a gel-like consistency and runs on the skin of its own accord even prior to manual distribution.

This comparative test shows a significant advantage of the gels of the invention, mainly that they form a high-viscosity creamy gel structure at low solids content, whereas the noninventive gels from comparative examples C1, C2, C4 and C5, which have been produced on the basis of an organopolysiloxane having a relatively high content of silicon-bonded hydrogen atoms, in spite of a higher solids content, do not form a gel-like structure and correspond to an oil in terms of their properties.

Example 41: Sensory Assessment of the Skincare Lotions from Examples 35, 36, 38 and 39

As example 40 showed, the noninventive comparative examples which have been produced on the basis of an organopolysiloxane having a relatively high content of silicon-bonded hydrogen atoms (comparative examples C1, C2, C4, and C5) are unsuitable for use in cosmetic products, since they do not have a suitable consistency or suitable sensory properties. For this reason, the materials were not included in the further assessment of the skincare lotions.

For the assessment of the skincare lotions from examples 35, 36, 38 and 39, the panelists applied 0.05 g in each case of the product to the cleaned lower arm over a circular area of 20 cm², and the lotions were compared with respect to their distributability relative to one another. After a wait time of 60 seconds, the residues of the organopolysiloxane gels were compared with respect to their silkiness relative to one another.

The skincare lotions from examples 35 and 36 use organopolysiloxane gels containing volatile linear polydimethylsiloxane (2 mm²/s at 25° C.) as diluent. The skincare lotions from examples 38 and 39 use organopolysiloxane gels containing nonvolatile linear polydimethylsiloxane (5 mm²/s at 25° C.) as diluent. Since this results in different characteristics in the application and in the residue, the products having different diluents were each assessed separately from one another.

According to the assessment of the panelists, both examples 35 and 36 have very good distributability. The residues of both examples were classified as silky by the majority. Example 36 was classified as being somewhat better compared to example 35 in terms of the silkiness of the residue.

TABLE 20

Sensory assessment of the skincare lotions from examples 35 and 36

| Example | containing 8% of example | Distributability | Silkiness |
|---|---|---|---|
| 35 | 5 | ++ | + |
| 36 | 6 | ++ | ++ |

According to the assessment of the panelists, both examples 38 and 39 have very good distributability. The residues of both examples were classified as silky by the majority. Example 39 was classified as being somewhat better compared to example 38 in both features.

TABLE 21

Sensory assessment of the skincare lotions from examples 38 and 39

| Example | containing 8% of example | Distributability | Silkiness |
|---|---|---|---|
| 38 | 8 | + | + |
| 39 | 13 | ++ | ++ |

The invention claimed is:

1. A composition comprising at least one organopolysiloxane gel having glycoside residues prepared by reacting:
   (1a) unsaturated organopolysiloxane resin(s) and
   (1b) compound(s) having a glycoside residue and a hydrosilylatable group,
   with the proviso that the proportion by weight of the compound (1b), based on the total weight of the organopolysiloxane gel, is 0.1% to 10% by weight,
   with
   (2) Si-H-functional organopolysiloxane(s) of the formula $$H_cR_{3-c}SiO(R_2SiO)_a(RHSiO)_bSiR_{3-c}H_c \quad (I)$$

where
   c is 0 or 1,
   R are the same or different and are monovalent, optionally substituted hydrocarbyl radicals having 1 to 18 carbon atoms per radical,
   a and b are integers, with the proviso that the sum of a+b is 66 to 248, wherein the organopolysiloxanes (2) contain Si-bonded hydrogen in amounts of 0.011% to 0.044% by weight, and the average number of Si-H groups per molecule is greater than 2 and less than 5, or mixtures of Si-H-functional organopolysiloxanes (2) with (2') Si-H-functional organopolysiloxanes of the formula $$H_cR_{3-c}SiO(R_2SiO)_a(RHSiO)_bSiR_{3-c}H_c \qquad (I')$$

where
c is 0 or 1,
R is as defined above,
a and b are integers, with the proviso that the sum of a+b is 8 to 248,
and the organopolysiloxanes (2') contain Si-bonded hydrogen in amounts of 0.045% to 0.35% by weight,
in the presence of
(3) catalysts that promote the addition of Si-bonded hydrogen onto aliphatic multiple bonds, where (1a) and (1b), and (2) or mixtures of (2) and (2') are dispersed in (4) diluent(s).

2. The composition of claim 1, wherein the diluent(s) comprise organopolysiloxanes having 2 to 200 silicon atoms or organic diluents or mixtures of organopolysiloxanes having 2 to 200 silicon atoms and organic diluents.

3. The composition of claim 1, wherein Si—H-functional organopolysiloxanes (2) contain Si-bonded hydrogen in an amount of 0.019-0.044 wt. %.

4. The composition of claim 1, wherein Si—H-functional organopolysiloxanes (2') contain Si-bonded hydrogen in an amount of 0.045-0.156 wt. %.

5. A creamy, storage-stable organopolysiloxane gel composition, prepared by homogenizing a composition of claim 1.

6. A creamy, storage-stable organopolysiloxane gel composition, prepared by homogenizing a composition of claim 1 in the presence of further diluent(s) (4) and/or active ingredients for personal care or healthcare.

7. The composition of claim 1, wherein
(1a) the unsaturated organopolysiloxane resins comprise MQ resins composed of units of the formulae $SiO_2$(Q units) and $R_3SiO_{1/2}$ and $R_2R'SiO_{1/2}$(M units), where
R are the same or different and are monovalent, optionally substituted hydrocarbyl radical having 1 to 18 carbon atoms per radical,
R' is a monovalent hydrocarbyl radical onto which may be added Si—H groups in a hydrosilylation reaction,
with the proviso that the MQ resins contain at least 2 R' radicals, and that the molar ratio of M units to Q units is in the range from 0.5 to 4.0.

8. The composition of claim 7, wherein the R' radicals comprise vinyl radicals.

9. The composition of claim 7, wherein the molar ratio of M units to Q units is from 0.5 to 2.0.

10. The composition of claim 1, wherein the compound(s) (1b) correspond to the formula $$Z—(R^1O)_p—R^2 \qquad (III)$$

where
Z is a glycoside residue formed from 1 to 10 monosaccharide units,
$R^1$ are the same or different and are divalent hydrocarbyl radicals having 2 to 4 carbon atoms,
$R^2$ are monovalent hydrocarbyl radicals having 2 to 12 carbon atoms, onto which may be added Si—H groups in a hydrosilylation reaction, and
p is 0 or an integer from 1 to 20.

11. The composition of claim 10, where Z is a glycoside residue comprising glucose units.

12. The composition of claim 10, wherein $R^2$ is a monovalent $C_{2-12}$ hydrocarbyl radical having a terminal aliphatic multiple C—C bond.

13. The composition of claim 1, wherein the diluent(s) (4) comprise polydimethylsiloxane(s) having 2 to 50 silicon atoms, aliphatic or alicyclic hydrocarbons having 4 to 30 carbon atoms, or esters of carboxylic acids having 2 to 30 carbon atoms.

14. The composition of claim 1, which is a monophasic homogeneous mixture comprising:
(a) organopolysiloxane gels having glycoside residues, and
(b) at least one polar or hydrophilic solvent.

15. The composition of claim 14, wherein the at least one polar or hydrophilic solvent (b) are selected from the group consisting of water, glycerol, ethylene glycol, diethylene glycol, propylene glycol, and mixtures thereof.

16. A process for producing a composition comprising at least one organopolysiloxane gel having glycoside residues of claim 1, comprising reacting
(1a) unsaturated organopolysiloxane resin(s) and
(1b) compound(s) having a glycoside residue and a hydrosilylatable end group,
with the proviso that the proportion by weight of compound(s) (1b), based on the total weight of the organopolysiloxane gel, is 0.1% to 10% by weight,
with
(2) Si—H-functional organopolysiloxane(s) of the formula $$H_cR_{3-c}SiO(R2SiO)_a(RHSiO)_bSiR_{3-c}H_c \qquad (I)$$

where
c is 0 or 1,
R are the same or different and are monovalent, optionally substituted hydrocarbyl radicals having 1 to 18 carbon atoms per radical,
a and b are integers, with the proviso that the sum of a+b is 66 to 248,
the organopolysiloxanes (2) contain Si-bonded hydrogen in amounts of 0.011% to 0.044% by weight,
and the average number of Si—H groups per molecule is greater than 2,
or mixtures of Si—H-functional organopolysiloxane(s) (2) with
(2') Si—H-functional organopolysiloxane(s) of the formula $$H_cR_{3-c}SiO(R_2SiO)_a(RHSiO)_bSiR_{3-c}H_c \qquad (I')$$

where
c is 0 or 1,
R is as defined above,
a and b are integers, with the proviso that the sum of a+b is 8 to 248,
and the organopolysiloxanes (2') contain Si-bonded hydrogen in amounts of 0.045% to 0.35% by weight,
in the presence of
(3) catalysts that promote the addition of Si-bonded hydrogen onto aliphatic multiple bonds, where (1a) and (1b), and (2) or mixtures of (2) and (2') are dispersed in (4) diluent(s).

17. The process of claim 16, wherein the diluent(s) comprise organopolysiloxanes having 2 to 200 silicon atoms or organic diluents or mixtures of organopolysiloxanes having 2 to 200 silicon atoms and organic diluents.

18. The process of claim 16, wherein the organopolysiloxane gels obtained after reacting are homogenized to form creamy, storage-stable organopolysiloxane gel compositions.

19. The process of claim 18, wherein the organopolysiloxane gels thus obtained are diluted with further diluent(s) (4) and/or active ingredients for personal care or healthcare, and then optionally homogenized.

20. The process of claim 16, wherein the
(1a) unsaturated organopolysiloxane resins comprise MQ resins composed of units of the formulae $SiO_2$(Q units) and $R_3SiO_{1/2}$ and $R_2R'SiO_{1/2}$(M units), R are the same or different and are monovalent, optionally substituted hydrocarbyl radical having 1 to 18 carbon atoms per radical, R' is a monovalent hydrocarbyl radical onto which may be added Si—H groups in a hydrosilylation reaction, with the proviso that the MQ resins contain at least 2 R' radicals, and that the molar ratio of M units to Q units is in the range from 0.5 to 4.0.

21. The process of claim 16, wherein the compound (1b) comprises a compound of the formula $Z-(R^1O)_p-R^2$ (III)

where

Z is a glycoside residue formed from 1 to 10 monosaccharide units, $R^1$ are the same or different and are divalent hydrocarbyl radicals having 2 to 4 carbon atoms, $R^2$ are monovalent hydrocarbyl radicals having 2 to 12 carbon atoms, onto which may be added Si—H groups in a hydrosilylation reaction, and p is 0 or an integer from 1 to 20.

22. The process of claim 16, wherein the diluent(s) (4) comprise at least one of polydimethylsiloxanes having 2 to 50 silicon atoms, aliphatic or alicyclic hydrocarbons having 4 to 30 carbon atoms, or esters of carboxylic acids having 2 to 30 carbon atoms.

23. A cosmetic composition, comprising at least one composition comprising organopolysiloxane gels having glycoside residues of claim 1.

24. A cosmetic composition, comprising at least one composition comprising organopolysiloxane gels having glycoside residues produced by the process of claim 16.

25. The composition of claim 1, wherein the weight ratio of organopolysiloxanes (2) to organopolysiloxanes (2') is greater than 0.2.

26. The composition of claim 1, wherein the weight ratio of organopolysiloxanes (2) to organopolysiloxanes (2') is greater than 0.5.

27. The composition of claim 1, wherein the weight ratio of organopolysiloxanes (2) to organopolysiloxanes (2') is greater than 1.

* * * * *